US007230132B2

(12) United States Patent
Ghosh et al.

(10) Patent No.: US 7,230,132 B2
(45) Date of Patent: Jun. 12, 2007

(54) ARYL N-CYANOGUANIDINES AND METHODS RELATED THERETO

(75) Inventors: Soumitra S Ghosh, San Diego, CA (US); Tomas R Szabo, La Mesa, CA (US)

(73) Assignee: Migenix Corp., San Diego, CA (US)

( * ) Notice: Subject to any disclaimer, the term of this patent is extended or adjusted under 35 U.S.C. 154(b) by 0 days.

(21) Appl. No.: 11/040,196

(22) Filed: Jan. 21, 2005

(65) Prior Publication Data

US 2005/0182057 A1 Aug. 18, 2005

Related U.S. Application Data

(63) Continuation of application No. 10/386,154, filed on Mar. 11, 2003, now Pat. No. 6,927,218, which is a continuation of application No. 10/085,119, filed on Feb. 27, 2002, now Pat. No. 6,562,821.

(60) Provisional application No. 60/272,368, filed on Feb. 27, 2001.

(51) Int. Cl.
C07C 279/28 (2006.01)
C07C 279/18 (2006.01)
(52) U.S. Cl. .................................... 564/104
(58) Field of Classification Search ................. 564/104
See application file for complete search history.

(56) References Cited

U.S. PATENT DOCUMENTS

| 4,265,905 | A | 5/1981 | Shen et al. ................. 424/304 |
| 4,654,342 | A | 3/1987 | Slater ......................... 514/247 |
| 6,562,821 | B2 * | 5/2003 | Ghosh et al. ............. 514/238.5 |
| 6,927,218 | B2 * | 8/2005 | Ghosh et al. ............. 514/238.5 |

FOREIGN PATENT DOCUMENTS

WO WO 01/72728 10/2001

OTHER PUBLICATIONS

Cunningham et al., Journal of the Chemical Society, Perkin Transactions 2 (1994), 8, p. 1849-1853.*
Database CAPLUS on STN, Acc. No. 1994:630233, Cunningham et al., Journal of the Chemical Society, Perkin Transactions 2 (1994), 8, p. 1849-1853 (abstract).*
Chen et al., "Regio- and stereoselective ring opening of epoxide with cyanoguanide dianions, a facile synthesis of the $K_{ATP}$ opener BMS-180448," *Tetrahedron: Asymmetry* 9:1337-1340, 1998.
Cunningham et al., "$^{13}$C and $^{15}$N NMR Study of Electron Distribution in N-Aryl-$N^1$-cyanoguanidines," *Magnetic Resonance in Chemistry* 34(3):221-226, 1996.
Cunningham et al., "Acidity and N-methylation of N-aryl-$N^1$-cyanoguanidines," *J. Chem. Soc., Perkin Trans.* 2(4):693-697, 1999.
Jones et al., "Lewis Acid Assisted Cyclization of Arylcyanoguanidines to 2,4-Diaminoquinazolines," *J. Heterocycl. Chem.* 31(6):1681-1683, 1994.
Kreutzberger et al., "2-Guanidino-4(3H)-chinazolinone mit chemotherapeutischen Eigenschaften," *Pharmazie* 48(1):17-20, 1993.
Kuyper et al., "High-Affinity Inhibitors of Dihydrofolate Reductase: Antimicrobial and Anticancer Activities of 7,8-Dialkyl-1,3-diaminopyrrolo[3,2-f]quinazolines with Small Molecular Size," *J. Med Chem.* 39:892-903, 1996.
Miller et al., "The Synthesis of Aminoiminoethanenitriles," 5-Aminotetrazoles, N-Cyanoguanidines and N-Hydorxyguanidines from Aminoiminomethanesulfonic acids, *Synthetic Communications* 20(2):217-226, 1990.
Stevens et al., "Potent and Selective Indolomorphinan Antagonists of the Kappa-Opioid Receptor," *J. Med. Chem.* 43:2759-2769, 2000.
Tilly et al., "The Synthesis of 3,5-Diamino-1,2,4-oxadiazoles," *Helvetica Chimica Acta* 63(4):841-859, 1980.
Database CAPLUS on STN, Acc. No. 1979:133326, Warner et al., J. Med. Chem. (1979), 22(4), p. 359-66 (abstract).
Database CAPLUS on STN, Acc. No. 1981:46923, Husain et al., Indian Drugs, (1980), 17(10), p. 315-17 (abstract).
Database CAPLUS on STN, Acc. No. 1986:34098, WO 8503076 (abstract), (1986).

* cited by examiner

*Primary Examiner*—Brian Davis
(74) *Attorney, Agent, or Firm*—Seed IP Law Group PLLC

(57) ABSTRACT

Compounds, compositions and methods treating arthritic disorders such as osteoarthritis or rheumatoid arthritis, and for treating other diseases associated with altered mitochondrial function, such as cancer, psoriasis, stroke, Alzheimer's Disease and diabetes. The compounds of this invention have the following structure (I):

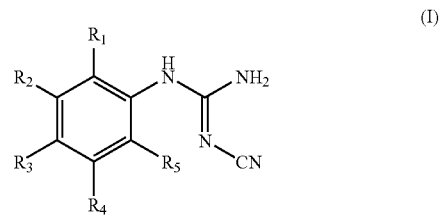

including stereoisomers, prodrugs and pharmaceutically acceptable salts thereof, wherein $R_{1-5}$ are as defined herein. The methods of this invention are directed to administering to a warm-blooded animal in need thereof an effective amount of a compound of structure (I), typically in the form of a pharmaceutical composition.

3 Claims, 1 Drawing Sheet

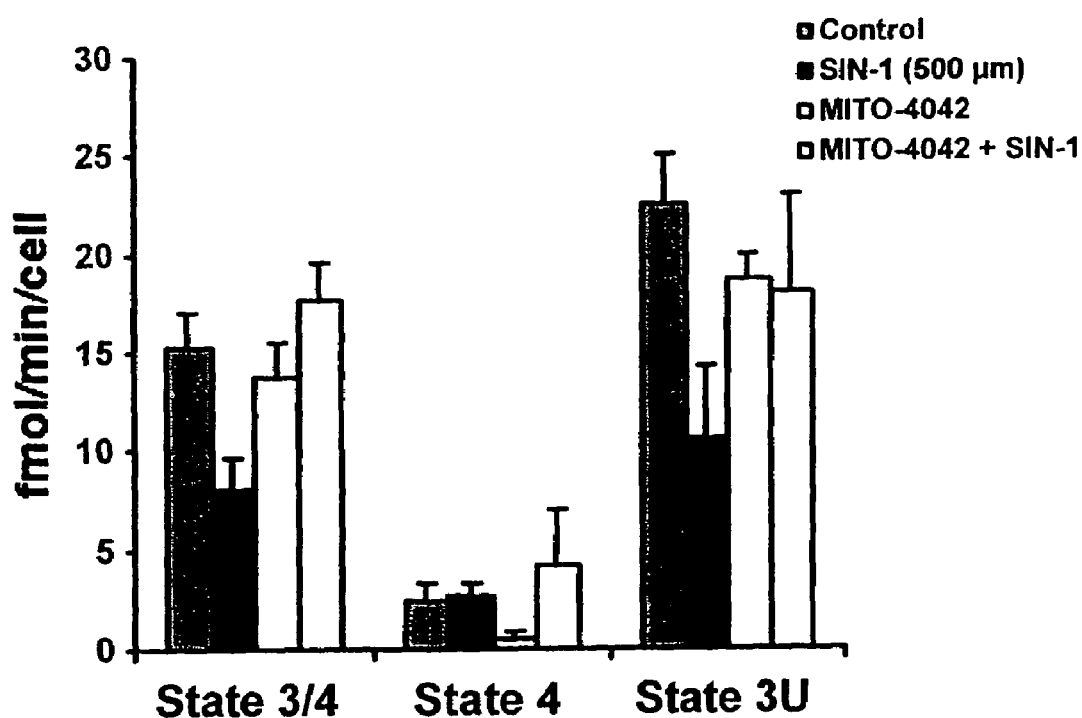

ARYL N-CYANOGUANIDINES AND METHODS RELATED THERETO

CROSS-REFERENCE TO RELATED APPLICATIONS

This application is a continuation of U.S. patent application Ser. No. 10/386,154, filed Mar. 11, 2003, now U.S. Pat. No. 6,927,218; which application is a continuation of U.S. patent application Ser. No. 10/085,119, filed Feb. 27, 2002, now U.S. Pat. No. 6,562,821; which application claims the benefit of U.S. Provisional Application No. 60/272,368 filed Feb. 27, 2001, all of which applications are incorporated herein by reference in their entireties.

TECHNICAL FIELD

The present invention relates generally to compounds and methods for treating arthritis and related disorders, and for treating diseases associated with altered mitochondrial function and, more particularly, to aryl N-cyanoguanidine compounds and derivatives thereof.

BACKGROUND OF THE INVENTION

Numerous chronic debilitating diseases of the skeletal system in vertebrates, including arthritis and related arthritic disorders, feature degradation of specialized avascular cartilaginous tissue known as articular cartilage that contains dedicated cartilage-producing cells, the articular chondrocytes. Unlike other chondrocytes such as epiphyseal growth plate chondrocytes present at the ends of developing long bones (e.g., endochondral or costochondral chondrocytes), articular chondrocytes reside in and maintain joint cartilage having no vasculature. Thus lacking a blood supply as an oxygen source, articular chondrocytes are believed to generate metabolic energy, for example bioenergetic ATP production, predominantly by anaerobic (e.g., glycolytic) respiration, and not from aerobic mitochondrial oxidative phosphorylation (Stefanovich-Racic et al., *J. Cell Physiol.* 159:274–80, 1994). Because even under aerobic conditions, articular chondrocytes may consume little oxygen and thus appear to differ from a wide variety of vertebrate cell types (Stefanoviceh-Racic et al., 1994), mitochondrial roles in arthritic disorders have been largely ignored.

The musculoskeletal system efficiently delivers useful mechanical energy and load support in vertebrates such as mammals, reptiles, birds and fish, but is also capable of synthesizing, processing and organizing complex macromolecules to fashion tissues and organs specialized to perform specific mechanical functions. The joints are an important subset of the specialized structures of the musculoskeletal system, and many distinct types of joints exist in the body. Freely moving joints (e.g., ankle, elbow, hip, knee, shoulder, and joints of the fingers, toes and wrist) are known as diarthrodial or synovial joints. In contrast, the intervertebral joints of the spine are not diarthrodial joints as they are fibrous and do not move freely, although they do provide the flexibility required by the spine. The articulating bone ends in the diarthrodial joint are lined with a thin layer of hydrated soft tissue known as articular cartilage. Fourth, the joint is stabilized by, and its range of motion controlled by, ligaments and tendons that may be inside or outside the joint capsule.

The surface linings of diarthrodial joints, i.e., the synovium and articular cartilage layers, form the joint cavity that contains the synovial fluid. Thus, in vertebrate skeletal joints, the synovial fluid, articular cartilage, and the supporting bone form a smooth, nearly frictionless bearing system. While diarthrodial joints are subjected to an enormous and varied range of load conditions, the cartilage surfaces undergo little wear and tear (e.g., structural degradation) under normal circumstances. Indeed, most human joints are capable of functioning effectively under very high loads and stresses and at very low operating speeds. These performance characteristics demand efficient lubrication processes to minimize friction and wear of cartilage in the joint. Severe breakdown of the joint cartilage by biochemical and/or biomechanical processes leads to arthritis, which is therefore generally defined as a failure of the vertebrate weight bearing system.

Articular chondrocytes synthesize and deposit the components of, and reside in, a three-dimensional cartilaginous extracellular matrix comprised largely of two major classes of macromolecules, collagen and proteoglycans. Articular chondrocytes thus mediate the synthesis, assembly, degradation and turnover of the macromolecules which comprise the cartilage extracellular matrix (ECM or simply "matrix"). Mechanochemical properties of this matrix contribute significantly to the biomechanical function of cartilage in vivo.

The structural integrity of articular cartilage is the foundation of optimal functioning of the skeletal joints, such as those found in the vertebrate hip, shoulders, elbows, hocks and stifles. Impaired skeletal joint function dramatically reduces an individual subject's mobility, such as that involved in rising from a sitting position or in climbing and descending stairs. As noted above, in order to maintain the structural and functional integrity of articular cartilage, articular chondrocytes constantly synthesize collagen and proteoglycans, the major components of the articular cartilage; chondrocytes also secrete the friction-reducing synovial fluid. This constant elaboration by articular chondrocytes of cartilage ECM macromolecules and synovial fluid provides the articular cartilage with a repair mechanism for most mechanical wear that may be caused by friction between the bone ends. However, such steady biosynthesis of cartilage components generates a constant demand for the precursors, or building blocks, of these macromolecules and synovial fluid components. Lack of these precursors will lead to defects in the structure and function of the skeletal joints. This deficiency occurs often when activity levels are very high, or when cartilage tissue is traumatized.

The menisci of the knee, and other similar structures such as the disc of the temporomandibular joint and the labrum of the shoulder, are specialized fibrocartilagenous structures that are vital for normal joint function. They are known to assist articular cartilage in distributing loads across the joint, to aid ligaments and tendons in stabilizing joints and to play a major role in shock absorption, and may further assist in lubricating the joint. Damage to these structures can lead to impaired joint function and to articular cartilage degeneration. Surgical removal of these fibrocartilagenous structures, for example, following apparently irreparable cartilage tears, can result in early onset of osteoarthritis. The menisci, disc and labrum are hydrated fibrocartilage structures composed primarily of type II collagen, with smaller amounts of other collagens and proteoglycans (including aggrecan and the smaller, non-aggregating proteoglycans) also present. These fibrocartilaginous structures contain a sparse population of resident cells that, like the articular chondrocytes of cartilage, are responsible for the synthesis and maintenance of this extracellular matrix.

Diarthrodial joints enable common bodily motions including limb movements associated with motor (e.g., ambulatory) functions and other activities of daily life. Failure of the joint surfaces (i.e., articular cartilage) means a failure of these biomechanical bearings to provide their central functions, such as ambulatory and other bodily motion, delivery of mechanical energy and load support.

In biomedical terms, failure of diarthrodial joints leads to arthritic disorders, the most common forms being osteoarthritis or degenerative joint disease, or chondrocalcinosis. Other forms of arthritic disorders include but are not limited to rheumatoid arthritis, juvenile rheumatoid arthritis, ankylosing spondylitis, Reiter's syndrome, psoriatic arthritis, lupus erythematosous, gout, infectious arthritides and chondrocalcinosis (see, e.g., Gilliland et al., "Disorders of the joints and connective tissue," Section 14, *Harrison's Principles of Internal Medicine*, Eighth Ed., Thorn et al., eds. McGraw-Hill, New York, N.Y., 1977, pp. 2048–80) and, in a veterinary context, dysplasias such as canine hip dysplasia. Arthritic disorders can also include, or may result from, physical trauma (for example, acute physical injury that damages joint tissue, or repetitive motion syndrome) or dietary conditions (e.g., ricketts or other dietary deficiency diseases) that result in joint injury.

By far, the most prevalent arthritic disorders are rheumatoid arthritis (RA) and osteoarthritis (OA). RA, thought to be an autoimmune disorder, results in part from inflammation of the synovial membrane. In humans, peak onset of this disorder occurs in adults over 30 years of age (typically in their thirties and forties) and afflicts women three times more often than men. In extreme cases, chronic inflammation erodes and distorts the joint surfaces and connective tissue, resulting in severe articular deformity and constant pain. Moreover, RA often leads to OA, further compounding the destruction of the joint. The most common arthritic disorder, OA, is characterized by degenerative changes in the surface of the articular cartilage. Alterations in the physicochemical structure of the cartilage make it less resistant to compressive and tensile forces. Finally, complete erosion occurs, leaving the subchondral bone exposed and susceptible to wear. Joints of the knees and hands are most often affected, as also may be one or more of the spine, hips, ankles and shoulders. In both RA and OA, degeneration of the weight bearing joints such as the hips and knees can be especially debilitating and often requires surgery to relieve pain, and to increase mobility.

No means currently exist for halting or reversing the degenerative changes brought about by RA, OA and related arthritic disorders. At the same time, approximately 37 million Americans seek symptomatic relief in the form of prescription drugs. In such cases nonsteroidal, anti-inflammatory drugs (NSAIDS) are most often prescribed. While these compounds often alleviate or palliate the arthritic symptoms, they frequently have undesirable side effects, for example, nausea and gastrointestinal ulceration. Other compounds commonly prescribed for the treatment of arthritic disorders are the corticosteroids, such as triamcinolone, prednisolone and hydrocortisone. These drugs also have undesirable side effects, particularly where long term use may be required, and so may be contraindicated in many patients. In addition to difficulties in determining effective dosages, a number of adverse reactions have been reported during intra-articular treatment with these and other steroids. As a result, the use of corticosteroid treatments in the management of arthritic disorders is currently being reassessed.

As an alternative to symptomatic and palliative measures for treating OA and RA as described above, mechanical repair of arthritic joints, when feasible, involves orthopedic surgery to replace worn joints with an artificial prosthesis, or with a biological graft. With more than thirty million Americans suffering from these disabling diseases, such surgery poses enormous medical and economic challenges and is not without its own risks and contraindications.

As noted above, osteoarthritis, also known as degenerative joint disease, is one of the most common types of arthritis. It is characterized by the breakdown of the cartilage within a joint, causing painful rubbing of one bone of the joint against another bone and leading to a loss of movement within the affected joint. Osteoarthritis can range from very mild to very severe, and most commonly affects middle-aged and older people. In particular, OA often affects hands and weight-bearing joints such as the knees, hips, feet and back. Although age is a leading risk factor, at present the etiology and pathogenesis of this condition remain largely unknown. Many environmental factors and other independent conditions have been associated with an increased risk for having or developing osteoarthritis, including obesity, previous injury and/or menisectomy (e.g., sports-related injuries or other accidental injury), occupation-related activities that involve repeated knee bending, smoking, sex hormones, gynecological disorders and other metabolic factors. Chondrocalcinosis is another form of degenerative joint disease related to osteoarthritis, in which abnormal calcification occurs in the articular cartilage.

From the foregoing, it is clear that none of the current pharmacological therapies corrects the underlying biochemical defect in arthritic disorders such as RA and OA. Neither do any of these currently available treatments improve all of the physiological abnormalities in arthritic disorders such as abnormal articular chondrocyte activity, cartilage degradation, articular erosion and severe joint deformity. In addition, treatment failures are common with these agents, such that multi-drug therapy is frequently necessary.

Clearly there is a need for improved therapeutics that are targeted to correct biochemical and/or metabolic defects responsible for arthritis. The present invention provides compositions and methods that are useful for treating an arthritic disorder and for treating other diseases, and offers other related advantages.

According to non-limiting theory, and as disclosed in the co-pending application having U.S. Ser. No. 09/661,848, which is incorporated by reference, some or all arthritic disorders as provided herein may represent examples of diseases associated with altered mitochondrial function.

By way of background, mitochondria are the main energy source in cells of higher organisms, and these organelles provide direct and indirect biochemical regulation of a wide array of cellular respiratory, oxidative and metabolic processes (for a review, see Ernster and Schatz, *J. Cell Biol.* 91:227s–255s, 1981). These include electron transport chain (ETC) activity, which drives oxidative phosphorylation to produce metabolic energy in the form of adenosine triphosphate (ATP), and which also underlies a central mitochondrial role in intracellular calcium homeostasis. In addition to their role in metabolic processes, mitochondria are also involved in the genetically programmed cell suicide sequence known as "apoptosis" (Green and Reed, *Science* 281:1309–12, 1998; Susin et al., *Biochim. et Biophys. Acta* 1366:151–65, 1998).

Defective mitochondrial activity, including but not limited to failure at any step of the elaborate multi-complex mitochondrial assembly, known as the electron transport chain (ETC), may result in (i) decreases in ATP production, (ii) increases in the generation of highly reactive free radicals (e.g., superoxide, peroxynitrite and hydroxyl radicals, and hydrogen peroxide), (iii) disturbances in intracellular calcium homeostasis and (iv) the release of factors (such as such as cytochrome c and "apoptosis inducing factor") that initiate or stimulate the apoptosis cascade. Because of these biochemical changes, mitochondrial dysfunction has the potential to cause widespread damage to cells and tissues.

A number of diseases and disorders are thought to be caused by or be associated with alterations in mitochondrial metabolism and/or inappropriate induction or suppression of mitochondria-related functions, such as those leading to apoptosis. These include, by way of example and not limitation, chronic neurodegenerative disorders such as Alzheimer's disease (AD) and Parkinson's disease (PD); autoimmune diseases; diabetes mellitus, including Type I and Type II; mitochondria associated diseases, including but not limited to congenital muscular-dystrophy with mitochondrial structural abnormalities, fatal infantile myopathy with severe mtDNA depletion and benign "later-onset" myopathy with moderate reduction in mtDNA, MELAS (mitochondrial encephalopathy, lactic acidosis, and stroke) and MIDD (mitochondrial diabetes and deafness); MERFF (myoclonic epilepsy ragged red fiber syndrome); arthritis; NARP (Neuropathy; Ataxia; Retinitis Pigmentosa); MNGIE (Myopathy and external ophthalmoplegia; Neuropathy; Gastro-Intestinal; Encephalopathy), LHON (Leber's; Hereditary; Optic; Neuropathy), Kearns-Sayre disease; Pearson's Syndrome; PEO (Progressive External Ophthalmoplegia); Wolfram syndrome DIDMOAD (Diabetes Insipidus, Diabetes Mellitus, Optic Atrophy, Deafness); Leigh's Syndrome; dystonia; schizophrenia; and hyperproliferative disorders, such as cancer, tumors and psoriasis. The extensive list of additional diseases associated with altered mitochondrial function continues to expand as aberrant mitochondrial or mitonuclear activities are implicated in particular disease processes.

According to generally accepted theories of mitochondrial function, proper ETC respiratory activity requires maintenance of an electrochemical potential ($\Delta\Psi m$) in the inner mitochondrial membrane by a coupled chemiosmotic mechanism. Conditions that dissipate or collapse this membrane potential, including but not limited to failure at any step of the ETC, may thus prevent ATP biosynthesis and hinder or halt the production of a vital biochemical energy source. Altered or defective mitochondrial activity may also result in a catastrophic mitochondrial collapse that has been termed "mitochondrial permeability transition" (MPT). In addition, mitochondrial proteins such as cytochrome c and "apoptosis inducing factor" may dissociate or be released from mitochondria due to MPT (or the action of mitochondrial proteins such as Bax), and may induce proteases known as caspases and/or stimulate other events in apoptosis (Murphy, *Drug Dev. Res.* 46:18–25, 1999).

Defective mitochondrial activity may alternatively or additionally result in the generation of highly reactive free radicals that have the potential of damaging cells and tissues. These free radicals may include reactive oxygen species (ROS) such as superoxide, peroxynitrite and hydroxyl radicals, and potentially other reactive species that may be toxic to cells. For example, oxygen free radical induced lipid peroxidation is a well established pathogenetic mechanism in central nervous system (CNS) injury such as that found in a number of degenerative diseases, and in ischemia (i.e., stroke). (Mitochondrial participation in the apoptotic cascade is believed to also be a key event in the pathogenesis of neuronal death.)

There are, moreover, at least two deleterious consequences of exposure to reactive free radicals arising from mitochondrial dysfunction that adversely impact the mitochondria themselves. First, free radical mediated damage may inactivate one or more of the myriad proteins of the ETC. Second, free radical mediated damage may result in catastrophic mitochondrial collapse that has been termed "transition permeability". According to generally accepted theories of mitochondrial function, proper ETC respiratory activity requires maintenance of an electrochemical potential in the inner mitochondrial membrane by a coupled chemiosmotic mechanism. Free radical oxidative activity may dissipate this membrane potential, thereby preventing ATP biosynthesis and/or triggering mitochondrial events in the apoptotic cascade. Therefore, by modulating these and other effects of free radical oxidation on mitochondrial structure and function, the present invention provides compositions and methods for protecting mitochondria that are not provided by the mere determination of free radical induced lipid peroxidation.

For example, rapid mitochondrial permeability transition likely entails changes in the inner mitochondrial transmembrane protein adenylate translocase that results in the formation of a "pore." Whether this pore is a distinct conduit or simply a widespread leakiness in the membrane is unresolved. In any event, because permeability transition is potentiated by free radical exposure, it may be more likely to occur in the mitochondria of cells from patients having mitochondria associated diseases that are chronically exposed to such reactive free radicals.

Altered (e.g., increased or decreased in a statistically significant manner relative to an appropriate control, such as a disease-free individual) mitochondrial function characteristic of the mitochondria associated diseases may also be related to loss of mitochondrial membrane electrochemical potential by mechanisms other than free radical oxidation, and such transition permeability may result from direct or indirect effects of mitochondrial genes, gene products or related downstream mediator molecules and/or extramitochondrial genes, gene products or related downstream mediators, or from other known or unknown causes. Loss of mitochondrial potential therefore may be a critical event in the progression of mitochondria associated or degenerative diseases.

Diabetes mellitus is a common, degenerative disease affecting 5 to 10 percent of the population in developed countries. The propensity for developing diabetes mellitus is reportedly maternally inherited, suggesting a mitochondrial genetic involvement. (Alcolado, J. C. and Alcolado, R., *Br. Med. J.* 302:1178–80, 1991; Reny, S. L., *International J. Epidem.* 23:886–90, 1994.) Diabetes is a heterogenous disorder with a strong genetic component; monozygotic twins are highly concordant and there is a high incidence of the disease among first-degree relatives of affected individuals.

At the cellular level, the degenerative phenotype that may be characteristic of late onset diabetes mellitus includes indicators of altered mitochondrial respiratory function, for example impaired insulin secretion, decreased ATP synthesis and increased levels of reactive oxygen species. Studies have shown that diabetes mellitus may be preceded by or associated with certain related disorders. For example, it is estimated that forty million individuals in the U.S. suffer from late onset impaired glucose tolerance (IGT). IGT patients fail to respond to glucose with increased insulin secretion. A small percentage of IGT individuals (5–10%) progress to insulin deficient non-insulin dependent diabetes (NIDDM) each year. Some of these individuals further progress to insulin dependent diabetes mellitus (IDDM). These forms of diabetes mellitus, NIDDM and IDDM, are associated with decreased release of insulin by pancreatic beta cells and/or a decreased end-organ response to insulin. Other symptoms of diabetes mellitus and conditions that precede or are associated with diabetes mellitus include obesity, vascular pathologies, peripheral and sensory neuropathies, blindness and deafness.

Due to the strong genetic component of diabetes mellitus, the nuclear genome has been the main focus of the search for causative genetic mutations. However, despite intense effort, nuclear genes that segregate with diabetes mellitus are known only for rare mutations in the insulin gene, the insulin receptor gene, the adenosine deaminase gene and the glucokinase gene. Accordingly, mitochondrial defects, which may include but need not be limited to defects related to the discrete non-nuclear mitochondrial genome that resides in mitochondrial DNA, may contribute significantly to the pathogenesis of diabetes mellitus (Anderson, *Drug Dev. Res.* 46:67–79, 1999).

Parkinson's disease (PD) is a progressive, chronic, mitochondria-associated neurodegenerative disorder characterized by the loss and/or atrophy of dopamine-containing neurons in the pars compacta of the substantia nigra of the brain. Like Alzheimer's Disease (AD), PD also afflicts the elderly. It is characterized by bradykinesia (slow movement), rigidity and a resting tremor. Although L-Dopa treatment reduces tremors in most patients for a while, ultimately the tremors become more and more uncontrollable, making it difficult or impossible for patients to even feed themselves or meet their own basic hygiene needs.

It has been shown that the neurotoxin 1-methyl-4-phenyl-1,2,3,6-tetrahydropyridine (MPTP) induces parkinsonism in animals and man at least in part through its effects on mitochondria. MPTP is converted to its active metabolite, MPP+, in dopamine neurons; it then becomes concentrated in the mitochondria. The MPP+ then selectively inhibits the mitochondrial enzyme NADH:ubiquinone oxidoreductase ("Complex I"), leading to the increased production of free radicals, reduced production of adenosine triphosphate, and ultimately, the death of affected dopamine neurons.

Mitochondrial Complex I is composed of 40–50 subunits; most are encoded by the nuclear genome and seven by the mitochondrial genome. Since parkinsonism may be induced by exposure to mitochondrial toxins that affect Complex I activity, it appears likely that defects in Complex I proteins may contribute to the pathogenesis of PD by causing a similar biochemical deficiency in Complex I activity. Indeed, defects in mitochondrial Complex I activity have been reported in the blood and brain of PD patients (Parker et al., *Am. J. Neurol.* 26:719–23, 1989; Swerdlow and Parker, *Drug Dev. Res.* 46:44–50, 1999).

Similar theories have been advanced for analogous relationships between mitochondrial defects and other neurological diseases, including Alzheimer's disease, Leber's hereditary optic neuropathy, schizophrenia, "mitochondrial encephalopathy, lactic acidosis, and stroke" (MELAS), and "myoclonic epilepsy ragged red fiber syndrome" (MERRF).

For example, Alzheimer's disease (AD) is a chronic, progressive neurodegenerative disorder that is characterized by loss and/or atrophy of neurons in discrete regions of the brain, and that is accompanied by extracellular deposits of β-amyloid and the intracellular accumulation of neurofibrillary tangles. It is a uniquely human disease, affecting over 13 million people worldwide. It is also a uniquely tragic disease. Many individuals who have lived normal, productive lives are slowly stricken with AD as they grow older, and the disease gradually robs them of their memory and other mental faculties. Eventually, they cease to recognize family and loved ones, and they often require continuous care until their eventual death.

There is evidence that defects in oxidative phosphorylation within the mitochondria are at least a partial cause of sporadic AD. The enzyme cytochrome c oxidase (COX), which makes up part of the mitochondrial electron transport chain (ETC), is present in normal amounts in AD patients; however, the catalytic activity of this enzyme in AD patients and in the brains of AD patients at autopsy has been found to be abnormally low. This suggests that the COX in AD patients is defective, leading to decreased catalytic activity that in some fashion causes or contributes to the symptoms that are characteristic of AD.

One hallmark pathology of AD is the death of selected neuronal populations in discrete regions of the brain. Cell death in AD is presumed to be apoptotic because signs of programmed cell death (PCD) are seen and indicators of active gliosis and necrosis are not found (Smale et al., *Exp. Neurolog.* 133:225–30, 1995; Cotman et al., *Molec. Neurobiol.* 10:19–45, 1995.) The consequences of cell death in AD, neuronal and synaptic loss, are closely associated with the clinical diagnosis of AD and are highly correlated with the degree of dementia in AD (DeKosky et al., *Ann. Neurol.* 27(5):467–64, 1990).

Mitochondrial dysfunction is thought to be critical in the cascade of events leading to apoptosis in various cell types (Kroemer et al., *FASEB J.* 9:1277–87, 1995), and may be a cause of apoptotic cell death in neurons of the AD brain. Altered mitochondrial physiology may be among the earliest events in PCD (Zamzami et al., *J. Exp. Med* 182:367–77, 1995; Zamzami et al., *J. Exp. Med.* 181:1661–72, 1995) and elevated reactive oxygen species (ROS) levels that result from such altered mitochondrial function may initiate the apoptotic cascade (Ausserer et al., *Mol. Cell. Biol.* 14:5032–42, 1994). In several cell types, including neurons, reduction in the mitochondrial membrane potential ($\Delta\Psi$m) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in mitochondria associated diseases and may further induce pathogenetic events via apoptotic mechanisms.

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al, *Biochim. Biophys. Act.* 1271:63, 1995). Localization of Bcl-2 to this membrane appears to be indispensable for modulation of apoptosis (Nguyen et al., *J. Biol. Chem.* 269:16521–24, 1994). Thus, changes in mitochondrial physiology may be important mediators of apoptosis. To the extent that apoptotic cell death is a prominent feature of neuronal loss in AD, mitochondrial dysfunction may be critical to the progression of this disease and may also be a contributing factor in other mitochondria associated diseases.

Focal defects in energy metabolism in the mitochondria, with accompanying increases in oxidative stress, may be associated with AD. It is well-established that energy metabolism is impaired in AD brain (Palmer et al., *Brain Res.* 645:338–42, 1994; Pappolla et al., *Am. J. Pathol.* 140:621–28, 1992; Jeandel et al., *Gerontol.* 35:275, 1989; Balazs et al., *Neurochem. Res.* 19:1131–37, 1994; Mecocci et al., *Ann. Neurol.* 36:747–51, 1994; Gsell et al., *J. Neurochem.* 64:1216–23, 1995). For example, regionally specific deficits in energy metabolism in AD brains have been reported in a number of positron emission tomography studies (Kuhl, et al., *J. Cereb. Blood Flow Metab.* 7:S406, 1987; Grady, et al., *J. Clin. Exp. Neuropsychol.* 10:576–96, 1988; Haxby et al., *Arch. Neurol.* 47:753–60, 1990; Azari et al., *J. Cereb. Blood Flow Metab.* 13:438–47, 1993). Metabolic defects in the temporoparietal neocortex of AD patients apparently presage cognitive decline by several years. Skin fibroblasts from AD patients display decreased glucose utilization and increased oxidation of glucose, leading to the formation of glycosylation end products (Yan et al., *Proc. Nat. Acad. Sci. U.S.A.* 91:7787–91, 1994). Cortical tissue from postmortem AD brain shows decreased activity of the mitochondrial enzymes pyruvate dehydrogenase (Sheu et al., *Ann. Neurol.* 17:444–49, 1985) and α-ketoglutarate dehydrogenase (Mastrogiacomo et al., *J. Neurochem.* 6:2007–14, 1994), which are both key enzymes in energy metabolism. Functional magnetic resonance spectroscopy studies have shown increased levels of inorganic phosphate relative to phosphocreatine in AD brain, suggesting an accumulation of precursors that arises from decreased ATP production by mitochondria (Pettegrew et al., *Neurobiol. of Aging* 15:117–32, 1994; Pettigrew et al., *Neurobiol. of Aging* 16:973–75, 1995). In addition, the levels of pyruvate, but not of glucose or lactate, are reported to be increased in the cerebrospinal fluid of AD patients, consistent with defects in cerebral mitochondrial electron transport chain (ETC) activity (Parnetti et al., *Neurosci. Lett.* 199:231–33, 1995).

Signs of oxidative injury are prominent features of AD pathology and, as noted above, reactive oxygen species (ROS) are critical mediators of neuronal degeneration. Indeed, studies at autopsy show that markers of protein, DNA and lipid peroxidation are increased in AD brain (Palmer et al., *Brain Res.* 645:338–42, 1994; Pappolla et al., *Am. J. Pathol.* 140:621–28, 1992; Jeandel et al., *Gerontol.* 35:275–82, 1989; Balazs et al., *Arch. Neurol.* 4:864, 1994; Mecocci et al., *Ann. Neurol.* 36:747–51, 1994; Smith et al., *Proc. Nat. Acad. Sci. U.S.A.* 88:10540–43, 1991). In hippocampal tissue from AD but not from controls, carbonyl formation indicative of protein oxidation is increased in neuronal cytoplasm, and nuclei of neurons and glia (Smith et al., *Nature* 382:120–21, 1996). Neurofibrillary tangles also appear to be prominent sites of protein oxidation (Schweers et al., *Proc. Nat. Acad. Sci. U.S.A.* 92:8463, 1995; Blass et al., *Arch. Neurol.* 4:864, 1990). Under stressed and non-stressed conditions incubation of cortical tissue from AD brains taken at autopsy demonstrate increased free radical production relative to non-AD controls. In addition, the activities of critical antioxidant enzymes, particularly catalase, are reduced in AD (Gsell et al., *J. Neurochem.* 64:1216–23, 1995), suggesting that the AD brain is vulnerable to increased ROS production. Thus, oxidative stress may contribute significantly to the pathology of mitochondria associated diseases such as AD, where mitochondrial dysfunction and/or elevated ROS may be present.

Increasing evidence points to the fundamental role of mitochondrial dysfunction in chronic neurodegenerative diseases (Beal, *Biochim. Biophys. Acta* 1366:211–23, 1998), and recent studies implicate mitochondria for regulating the events that lead to necrotic and apoptotic cell death (Susin et al., *Biochim. Biophys. Acta* 1366:151–68, 1998). Stressed (by, e.g., free radicals, high intracellular calcium, loss of ATP, among others) mitochondria may release pre-formed soluble factors that can initiate apoptosis through an interaction with apoptosomes (Marchetti et al., *Cancer Res.* 56:2033–38, 1996; Li et al., *Cell* 91:479–89, 1997). Release of preformed soluble factors by stressed mitochondria, like cytochrome c, may occur as a consequence of a number of events. In any event, it is thought that the magnitude of stress (ROS, intracellular calcium levels, etc.) influences the changes in mitochondrial physiology that ultimately determine whether cell death occurs via a necrotic or apoptotic pathway. To the extent that apoptotic cell death is a prominent feature of degenerative diseases, mitochondrial dysfunction may be a critical factor in disease progression.

In contrast to chronic neurodegenerative diseases, neuronal death following stroke occurs in an acute manner. A vast amount of literature now documents the importance of mitochondrial function in neuronal death following ischemia/reperfusion injury that accompanies stroke, cardiac arrest and traumatic injury to the brain. Experimental support continues to accumulate for a central role of defective energy metabolism, alteration in mitochondrial function leading to increased oxygen radical production and impaired intracellular calcium homeostasis, and active mitochondrial participation in the apoptotic cascade in the pathogenesis of acute neurodegeneration.

A stroke occurs when a region of the brain loses perfusion and neurons die acutely or in a delayed manner as a result of this sudden ischemic event. Upon cessation of the blood supply to the brain, tissue ATP concentration drops to negligible levels within minutes. At the core of the infarct, lack of mitochondrial ATP production causes loss of ionic homeostasis, leading to osmotic cell lysis and necrotic death. A number of secondary changes can also contribute to cell death following the drop in mitochondrial ATP. Cell death in acute neuronal injury radiates from the center of an infarct where neurons die primarily by necrosis to the penumbra where neurons undergo apoptosis to the periphery where the tissue is still undamaged (Martin et al., *Brain Res. Bull.* 46:281–309, 1998).

Much of the injury to neurons in the penumbra is caused by excitotoxicity induced by glutamate released during cell lysis at the infarct focus, especially when exacerbated by bioenergetic failure of the mitochondria from oxygen deprivation (MacManus and Linnik, *J. Cerebral Blood Flow Metab.* 17:815–32, 1997). The initial trigger in excitotoxicity is the massive influx of $Ca^{2+}$ primarily through the NMDA receptors, resulting in increased uptake of $Ca^{2+}$ into the mitochondria (reviewed by Dykens, "Free radicals and mitochondrial dysfunction in excitotoxicity and neurodegenerative diseases" in *Cell Death and Diseases of the Nervous System*, V. E. Koliatos and R. R. Ratan, eds., Humana Press, New Jersey, pp. 45–68, 1999). The $Ca^{2+}$ overload collapses the mitochondrial membrane potential ($\Delta\Psi_m$) and induces increased production of reactive oxygen species (Dykens, *J Neurochem* 63:584–91, 1994; Dykens, "Mitochondrial radical production and mechanisms of oxidative excitotoxicity" in *The Oxygen Paradox*, K. J. A. Davies, and F. Ursini, eds., Cleup Press, U. of Padova, pages 453–67, 1995). If severe enough, $\Delta\Psi_m$ collapse and mitochondrial $Ca^{2+}$ sequestration can induce opening of a pore in the inner mitochondrial membrane through a process called mitochondrial permeability transition (MPT), indirectly releasing cytochrome c and other proteins that initiate apoptosis (Bernardi et al., *J. Biol. Chem.* 267:2934–39, 1994; Zoratti and Szabo, *Biochim. Biophys. Acta* 1241:139–76, 1995; Ellerby et al., *J Neurosci* 17:6165–78, 1997). Consistent with these observations, glutamate-induced excitotoxicity can be inhibited by preventing mitochondrial $Ca^{2+}$ uptake or blocking MPT (Budd and Nichols, *J Neurochem* 66:403–11, 1996; White and Reynolds, *J Neurosci* 16:5688–97, 1996; Li et al., *Brain Res*. 753:133–40, 1997).

Whereas mitochondria-mediated apoptosis may be critical in degenerative diseases, it is thought that disorders such as cancer involve the unregulated and undesirable growth (hyperproliferation) of cells that have somehow escaped a mechanism that normally triggers apoptosis in such undesirable cells. Enhanced expression of the anti-apoptotic protein, Bcl-2 and its homologues is involved in the pathogenesis of numerous human cancers. Bcl-2 acts by inhibiting programmed cell death and overexpression of Bcl-2, and the related protein Bcl-xL, block mitochondrial release of cytochrome c from mitochondria and the activation of caspase 3 (Yang et al, *Science* 275:1129–32, 1997; Kluck et al., *Science* 275:1132–36, 1997; Kharbanda et al., *Proc. Natl. Acad. Sci. USA*. 94:6939–42, 1997). In contrast, overexpression of Bcl-2 and Bcl-xL protect against the mitochondrial dysfunction preceding nuclear apoptosis that is induced by chemotherapeutic agents. In addition, acquired multi-drug resistance to cytotoxic drugs is associated with inhibition cytochrome c release that is dependent on overexpression of Bcl-xL (Kojima et al., *J. Biol. Chem*. 273:16647–50, 1998). Because mitochondria have been implicated in apoptosis, it is expected that agents that interact with mitochondrial components will effect a cell's capacity to undergo apoptosis. Thus, agents that induce or promote apoptosis in hyperproliferative cells are expected to be useful in treating hyperproliferative disorders and diseases such as cancer.

Thus, alteration of mitochondrial function has great potential for a broad-based therapeutic strategy for designing drugs to treat diseases associated with altered mitochondrial function, including (by way of non-limiting theory) certain arthritic disorders, degenerative disorders and hyperproliferative diseases. Further according to non-limiting theory, depending on the disease or disorder for which treatment is sought, such drugs may be, for example, mitochondria protecting agents, anti-apoptotic agents or pro-apoptotic agents.

Clearly there is a need for compounds and methods that limit or prevent damage to organelles, cells and tissues that results directly or indirectly from mitochondrial dysfunction, for example damage by free radicals generated intracellularly. In particular, because mitochondria are essential organelles for producing metabolic energy, agents that protect mitochondria against such damage (e.g., oxidative injury by free radicals) would be especially useful. Such agents may be suitable for the treatment of degenerative diseases including mitochondria associated diseases. Existing approaches to identifying agents that limit oxidative damage may not include determination of whether such agents may help protect mitochondrial structure and/or function.

There is also a need for compounds and methods that limit or prevent damage to cells and tissues that occurs directly or indirectly as a result of necrosis and/or inappropriate apoptosis. In particular, because mitochondria are mediators of apoptotic events, agents that modulate mitochondrially mediated pro-apoptotic events would be especially useful. Such agents may be suitable for the treatment of acute degenerative events such as stroke. Given the limited therapeutic window for blockade of necrotic death at the core of an infarct, it may be particularly desirable to develop therapeutic strategies to limit neuronal death by preventing mitochondrial dysfunction in the non-necrotic regions of an infarct. Agents and methods that maintain mitochondrial integrity during transient ischemia and the ensuing wave of excitotoxicity would be expected to be novel neuroprotective agents with utility in limiting stroke-related neuronal injury.

There is also a need for compounds and methods that inhibit the growth or enhance the death of cells and tissues that have escaped appropriate apoptotic signals, as well as cytotoxic agents that cause the death of undesirable (e.g., cancer) cells by triggering the apoptotic cascade. In particular, because mitochondria are mediators of apoptotic events, agents that stimulate mitochondrially mediated pro-apoptotic events would be especially useful. Such agents may be suitable for the treatment of hyperproliferative diseases such as cancer and psoriasis.

The present invention fulfills these needs and provides other related advantages. Those skilled in the art will recognize further advantages and benefits of the invention after reading the disclosure.

SUMMARY OF THE INVENTION

Briefly stated, the present invention is directed to the treatment of an arthritic disorder and/or to the treatment of a disease associated with altered mitochondrial function by administration to a warm-blooded animal in need thereof an effective amount of a compound having the following general structure (I):

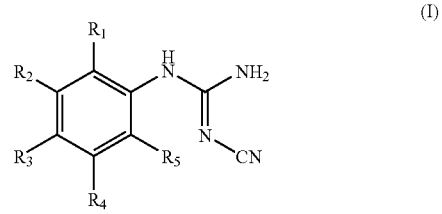

including stereoisomers, prodrugs and pharmaceutically acceptable salts thereof, wherein $R_1$ through $R_5$ are as defined below.

In certain embodiments, the invention provides a pharmaceutical composition comprising an aryl N-cyanoguanidine compound of structure (I) and a pharmaceutically acceptable carrier. According to other embodiments, the invention provides a method for treating an arthritic disorder, by administering an effective amount of such a pharmaceutical composition to an animal in need thereof. According to still further embodiments, there is provided a method for treating a disease associated with altered mitochondrial function comprising administering an effective amount of such a pharmaceutical composition to an animal in need thereof.

These and other aspects of the present invention will become evident upon reference to the following detailed description. In addition, various references are set forth herein which describe in more detail certain aspects of this invention, and are therefore incorporated by reference in their entireties.

BRIEF DESCRIPTION OF THE DRAWING

FIG. 1 illustrates the ability of a representative compound to block SIN-1-mediated inhibition of mitochondrial respiration in TC28 cells.

DETAILED DESCRIPTION OF THE INVENTION

The present invention provides compounds, compositions and methods that are useful in treatment of arthritic disorders and/or of diseases associated with altered mitochondrial function. More specifically, the compounds of this invention have the following structure (I):

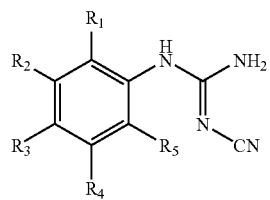

(I)

or a stereoisomer, prodrug or pharmaceutically acceptable salt thereof, wherein $R_1$, $R_2$, $R_3$, $R_4$ and $R_5$ are the same or different and individually hydrogen, halogen, hydroxy, alkyl, alkoxy, substituted alkyl, aryl, substituted aryl, arylalky, substituted arylalkyl, heterocycle, substituted heterocycle, heterocyclealkyl or substituted heterocyclealkyl; or $R_3$ taken together with $R_4$, or $R_4$ taken together with $R_5$, and further taken together with the respective carbon atom to which these groups are attached, form an unsubstituted or substituted fused aryl or heterocycle.

As used herein, the above terms have the following meanings:

"Alkyl" means a straight chain or branched, noncyclic or cyclic, unsaturated or saturated aliphatic hydrocarbon containing from 1 to 10 carbon atoms, while the term "lower alkyl" has the same meaning as alkyl but contains from 1 to 6 carbon atoms. Representative saturated straight chain alkyls include methyl, ethyl, n-propyl, n-butyl, n-pentyl, n-hexyl, and the like; while saturated branched alkyls include isopropyl, sec-butyl, isobutyl, tert-butyl, isopentyl, and the like. Representative saturated cyclic alkyls include cyclopropyl, cyclobutyl, cyclopentyl, cyclohexyl, —CH$_2$cyclopropyl, —CH$_2$cyclobutyl, —CH$_2$cyclopentyl, —CH$_2$cyclohexyl, and the like; while unsaturated cyclic alkyls include cyclopentenyl and cyclohexenyl, and the like. Cyclic alkyls, also referred to as "homocyclic rings," and include di- and poly-homocyclic rings such as decalin and adamantyl. Unsaturated alkyls contain at least one double or triple bond between adjacent carbon atoms (referred to as an "alkenyl" or "alkynyl", respectively). Representative straight chain and branched alkenyls include ethylenyl, propylenyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, and the like; while representative straight chain and branched alkynyls include acetylenyl, propynyl, 1-butynyl, 2-butynyl, 1-pentynyl, 2-pentynyl, 3-methyl-1 butynyl, and the like.

"Aryl" means an aromatic carbocyclic moiety such as phenyl or naphthyl.

"Arylalkyl" means an alkyl having at least one alkyl hydrogen atoms replaced with an aryl moiety, such as benzyl, —CH2-(1 or 2-naphthyl), —(CH2)2phenyl, —(CH2)3phenyl, —CH(phenyl)2, and the like.

"Heteroaryl" means an aromatic heterocycle ring of 5- to 10 members and having at least one heteroatom selected from nitrogen, oxygen and sulfur, and containing at least 1 carbon atom, including both mono- and bicyclic ring systems. Representative heteroaryls include (but are not limited to) furyl, benzofuranyl, thiophenyl, benzothiophenyl, pyrrolyl, indolyl, isoindolyl, azaindolyl, pyridyl, quinolinyl, isoquinolinyl, oxazolyl, isooxazolyl, benzoxazolyl, pyrazolyl, imidazolyl, benzimidazolyl, thiazolyl, benzothiazolyl, isothiazolyl, pyridazinyl, pyrimidinyl, pyrazinyl, triazinyl, cinnolinyl, phthalazinyl, and quinazolinyl.

"Heteroarylalkyl" means an alkyl having at least one alkyl hydrogen atom replaced with a heteroaryl moiety, such as —CH$_2$pyridinyl, —CH$_2$pyrimidinyl, and the like.

"Heterocycle" (also referred to herein as a "heterocycle ring") means a 5- to 7-membered monocyclic, or 7- to 14-membered polycyclic, heterocycle ring which is either saturated, unsaturated or aromatic, and which contains from 1 to 4 heteroatoms independently selected from nitrogen, oxygen and sulfur, and wherein the nitrogen and sulfur heteroatoms may be optionally oxidized, and the nitrogen heteroatom may be optionally quaternized, including bicyclic rings in which any of the above heterocycles are fused to a benzene ring as well as tricyclic (and higher) heterocyclic rings. The heterocycle may be attached via any heteroatom or carbon atom. Heterocycles include heteroaryls as defined above. Thus, in addition to the aromatic heteroaryls listed above, heterocycles also include (but are not limited to) morpholinyl, pyrrolidinonyl, pyrrolidinyl, piperidinyl, hydantoinyl, valerolactamyl, oxiranyl, oxetanyl, tetrahydrofuranyl, tetrahydropyranyl, tetrahydropyridinyl, tetrahydroprimidinyl, tetrahydrothiophenyl, tetrahydrothiopyranyl, tetrahydropyrimidinyl, tetrahydrothiophenyl, tetrahydrothiopyranyl, and the like.

"Heterocyclealkyl" means an alkyl having at least one alkyl hydrogen atom replaced with a heterocycle, such as —CH$_2$morpholinyl, and the like.

The term "substituted" as used herein means any of the above groups (e.g., alkyl, aryl, arylalkyl, heteroaryl, heteroarylalkyl, heterocycle, heterocyclealkyl, etc.) wherein at least one hydrogen atom is replaced with a substituent. In the case of a keto substituent ("=O") two hydrogen atoms are replaced. When substituted, "substituents" within the context of this invention include halogen, hydroxy, cyano, nitro, amino, alkylamino, dialkylamino, alkyl, alkoxy, alkylthio, haloalkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocyclealkyl, substituted heterocyclealkyl, —NR$_a$R$_b$, —NR$_a$C(=O)R$_b$, —NR$_a$C(=O)NR$_a$NR$_b$, —NR$_a$C(=O)OR$_b$ —NR$_a$SO$_2$R$_b$, —OR$_a$, —C(=O)R$_a$ —C(=O)OR$_a$, —C(=O)NR$_a$R$_b$, —OC(=O)NR$_a$R$_b$, —SH, SR$_a$, —SOR$_a$, —S(=O)$_2$R$_a$, —OS(=O)$_2$R$_a$, —S(=O)$_2$OR$_a$, wherein R$_a$ and R$_b$ are the same or different and independently hydrogen, alkyl, haloalkyl, substituted alkyl, aryl, substituted aryl, arylalkyl, substituted arylalkyl, heteroaryl, substituted heteroaryl, heteroarylalkyl, substituted heteroarylalkyl, heterocycle, substituted heterocycle, heterocylealkyl or substituted heterocyclealkyl. For example, substituted alkyl includes trifluoromethyl.

"Halogen" means fluoro, chloro, bromo and iodo.

"Haloalkyl" means an alkyl having at least one hydrogen atom replaced with halogen, such as trifluoromethyl and the like.

"Alkoxy" means an alkyl moiety attached through an oxygen bridge (i.e., —O-alkyl) such as methoxy, ethoxy, and the like.

In more specific embodiment of this invention, at least two of $R_1$ through $R_5$ are hydrogen, an in another embodiment at least three of $R_1$ through $R_5$ are hydrogen, and in still another embodiment at least four of $R_1$ through $R_5$ are hydrogen.

In a further embodiment, $R_1$ through $R_5$ are the same or different and independently hydrogen, alkyl, substituted alkyl, hydroxyl, halogen or alkoxy, wherein representative alkyl includes methyl, representative alkoxy includes methoxy and representative substituted alkyl includes trifluoromethyl.

In another embodiment, at least one of $R_1$ through $R_5$ is a heterocycle, such as morpholinyl.

In yet a further embodiment, $R_3$ taken together with $R_4$, or $R_4$ taken together with $R_5$, and further taken together with the respective carbon atom to which these groups are attached, form an unsubstituted or substituted fused aryl or heterocycle. For example, in the case of an unsubstituted or substituted aryl, representative compounds of this invention have the following structure (II) when $R_4$ and $R_5$ taken together form a fused aryl, and structure (III) when $R_3$ and $R_4$ taken together form a fused aryl:

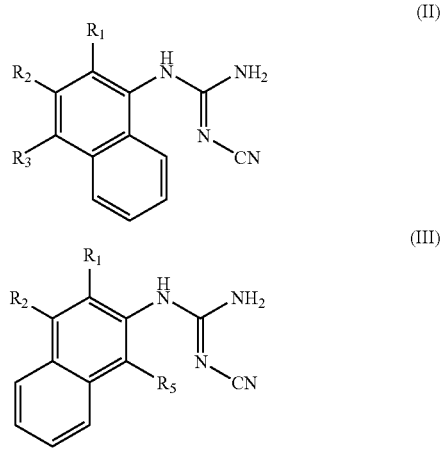

wherein the fused aryl portion of structure (II) or (III) may be optionally substituted by one or more substituents as defined above.

The compounds of the present invention may be prepared by known organic synthesis techniques, including the methods described in more detail in the Examples. In general, the compounds of this invention may be prepared by the following Reaction Scheme:

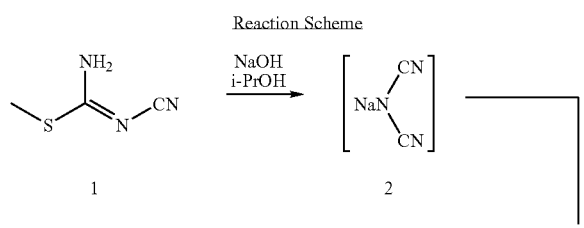

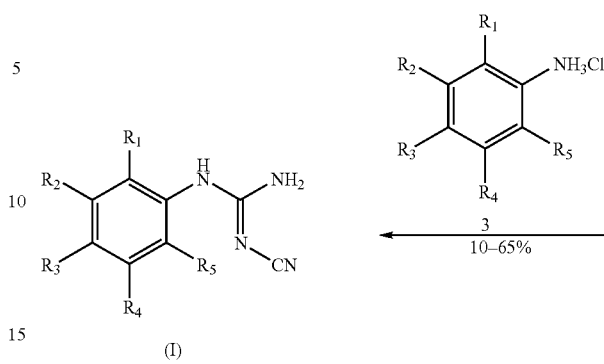

In the above Reaction Scheme, N-cyano-S-methylisothiourea 1 is dissolved in i-PrOH, followed by addition of NaOH. The resulting solution is heated and then cooled to generate the intermediate salt, sodium dicyanamide 2. This intermediate salt is then added to the appropriately-substituted analine 3 in HCl. The reaction mixture is heated, cooled and then evaporated to yield a compound of structure (I) as a crude product, which may then be purified to yield to a compound of structure (I) having the desired purity.

As noted above, clinical parameters and criteria for determining the presence or risk of an arthritic disorder are well established (e.g., Gilliland et al., "Disorders of the joints and connective tissue," Section 14, *Harrison's Principles of Internal Medicine*, Eighth Ed., Thorn et al., eds. McGraw-Hill, New York, N.Y., 1977, pp. 2048–2080), as are criteria for determining the presence or risk of a number of other diseases associated with altered mitochondrial function, as also provided herein (e.g., for AD, McKhann et al., *Neurology* 34:939, 1984; DeKosky et al., *Ann. Neurology* 27(5): 467–64, 1990; for diabetes, Gavin et al., *Diabetes Care* 22(suppl. 1):S5–S19, 1999; etc.—other diagnostic criteria for diseases associated with altered mitochondrial function will be familiar to those having ordinary skill in the art and based on the disclosure herein). "Altered mitochondrial function" may refer to any condition or state, including those that may, according to non-limiting theory, accompany an arthritic disorder, where any structure or activity that is directly or indirectly related to a mitochondrial function has been changed in a statistically significant manner relative to a control or standard. Altered mitochondrial function may have its origin in extramitochondrial structures or events as well as in mitochondrial structures or events, in direct interactions between mitochondrial and extramitochondrial genes and/or their gene products, or in structural or functional changes that occur as the result of interactions between intermediates that may be formed as the result of such interactions, including metabolites, catabolites, substrates, precursors, cofactors and the like.

Additionally, altered mitochondrial function may include altered respiratory, metabolic or other biochemical or biophysical activity in some or all cells of a biological source. As non-limiting examples, markedly impaired ETC activity may be related to altered mitochondrial function, as may be generation of increased reactive oxygen species (ROS) or defective oxidative phosphorylation. As further examples, altered mitochondrial membrane potential (e.g., PCT/US99/22261; PCT/US00/17380), altered mitochondrial regulation of intracellular calcium homeostasis (e.g., U.S. Pat. No. 6,140,067), induction of apoptotic pathways and formation of atypical chemical and biochemical crosslinked species within a cell, whether by enzymatic or non-enzymatic mechanisms, may all be regarded as indicative of altered mitochondrial function. These and other non-limiting examples of altered mitochondrial function are described in greater detail below.

Without wishing to be bound by theory, altered mitochondrial function that may be characteristic of an arthritic disorder or of another disease associated with altered mitochondrial function, as provided herein, may also be related to loss of mitochondrial membrane electrochemical potential by mechanisms other than free radical oxidation, for example by defects in transmitochondrial membrane shuttles and transporters such as the mitochondrial adenine nucleotide transporter or the malate-aspartate shuttle, by intracellular calcium flux, by defects in ATP biosynthesis, by impaired association with mitochondrial porin (also known, e.g., as voltage dependent anion channel, VDAC) of hexokinases or other enzymes or by other events. Such collapse of mitochondrial inner membrane potential may result from direct or indirect effects of mitochondrial genes, gene products or related downstream mediator molecules and/or extramitochondrial genes, gene products or related downstream mediators, or from other known or unknown causes.

By way of background, functional mitochondria contain gene products encoded by mitochondrial genes situated in mitochondrial DNA (mtDNA) and by extramitochondrial genes (e.g., nuclear genes) not situated in the circular mitochondrial genome. The 16.5 kb mtDNA encodes 22 tRNAs, two ribosomal RNAs (rRNA) and 13 enzymes of the electron transport chain (ETC), the elaborate multi-complex mitochondrial assembly where, for example, respiratory oxidative phosphorylation takes place. The overwhelming majority of mitochondrial structural and functional proteins are encoded by extramitochondrial, and in most cases presumably nuclear, genes. Accordingly, mitochondrial and extramitochondrial genes may interact directly, or indirectly via gene products and their downstream intermediates, including metabolites, catabolites, substrates, precursors, cofactors and the like. Alterations in mitochondrial function, for example impaired electron transport activity, defective oxidative phosphorylation or increased free radical production, may therefore arise as the result of defective mtDNA, defective extramitochondrial DNA, defective mitochondrial or extramitochondrial gene products, defective downstream intermediates or a combination of these and other factors.

According to certain embodiments of the present invention, as it relates to an arthritic disorder and/or a disease associated with altered mitochondrial function, determination of altered (e.g., increased or decreased in a statistically significant manner relative to a control) mitochondrial function may involve monitoring intracellular calcium homeostasis and/or cellular responses to perturbations of this homeostasis, including physiological and pathophysiological calcium regulation. In particular, according to these embodiments, a cellular response to elevated intracellular calcium in a biological sample from a subject known or suspected of having a disease associated with altered mitochondrial function is compared to the response in a biological sample from a control subject. The range of cellular responses to elevated intracellular calcium is broad, as is the range of methods and reagents for the detection of such responses. Many specific cellular responses are known to those having ordinary skill in the art; these responses will depend on the particular cell types present in a selected biological sample. As non-limiting examples, cellular responses to elevated intracellular calcium include secretion of specific secretory products, exocytosis of particular preformed components, increased glycogen metabolism and cell proliferation (see, e.g., Clapham, Cell 80:259, 1995; Cooper, The Cell—A Molecular Approach, 1997 ASM Press, Washington, D.C.; Alberts, B., Bray, D., et al., Molecular Biology of the Cell, 1995 Garland Publishing, NY).

As a brief background, normal alterations of intramitochondrial $Ca^{2+}$ are associated with normal metabolic regulation (Dykens, 1998 in Mitochondria & Free Radicals in Neurodegenerative Diseases, Beal, Howell and Bodis-Wollner, Eds., Wiley-Liss, New York, pp. 29–55; Radi et al., 1998 in Mitochondria & Free Radicals in Neurodegenerative Diseases, Beal, Howell and Bodis-Wollner, Eds., Wiley-Liss, New York, pp. 57–89; Gunter and Pfeiffer, Am. J. Physiol. 27:C755, 1991; Gunter et al., Am. J. Physiol. 267:313, 1994). For example, fluctuating levels of mitochondrial free $Ca^{2+}$ may be responsible for regulating oxidative metabolism in response to increased ATP utilization, via allosteric regulation of enzymes (reviewed by Crompton et al., Basic Res. Cardiol. 88:513–23, 1993) and the glycerophosphate shuttle (Gunter et al., J Bioenerg. Biomembr. 26:471, 1994).

Normal mitochondrial function includes regulation of cytosolic free calcium levels by sequestration of excess $Ca^{2+}$ within the mitochondrial matrix. Depending on cell type, cytosolic $Ca^{2+}$ concentration is typically 50–100 nM. In normally functioning cells, when $Ca^{2+}$ levels reach 200–300 nM, mitochondria begin to accumulate $Ca^{2+}$ as a function of the equilibrium between influx via a $Ca^{2+}$ uniporter in the inner mitochondrial membrane and $Ca^{2+}$ efflux via both $Na^+$ dependent and $Na^+$ independent calcium carriers. In certain instances, such perturbation of intracellular calcium homeostasis is a feature of diseases associated with altered mitochondrial function, regardless of whether the calcium regulatory dysfunction is causative of, or a consequence of, altered mitochondrial function.

Elevated mitochondrial calcium levels thus may accumulate in response to an initial elevation in cytosolic free calcium, as described above. Such elevated mitochondrial calcium concentrations in combination with reduced ATP or other conditions associated with mitochondrial pathology, can lead to collapse of mitochondrial inner membrane potential (see Gunter et al., Biochim. Biophys. Acta 1366:5, 1998; Rottenberg and Marbach, Biochim. Biophys. Acta 1016:87, 1990). Generally, the extramitochondrial (cytosolic) level of $Ca^{2+}$ in a biological sample is greater than that present within mitochondria. In the case of a disease associated with altered mitochondrial function, mitochondrial or cytosolic calcium levels may vary from the above ranges and may range from, e.g., about 1 nM to about 500 mM, more typically from about 10 nM to about 100 µM and usually from about 20 nM to about 1 µM, where "about" indicates ±10%. A variety of calcium indicators are known in the art, including but not limited to, for example, fura-2 (McCormack et al., Biochim. Biophys. Acta 973:420, 1989); mag-fura-2; BTC (U.S. Pat. No. 5,501,980); fluo-3, fluo-4 and fluo-5N (U.S. Pat. No. 5,049,673); rhod-2; benzothiaza-1; and benzothiaza-2 (all of which are available from Molecular Probes, Eugene, Oreg.). These or any other means for monitoring intracellular calcium are contemplated for determining the presence of altered mitochondrial function (see, e.g., PCT/US01/01500).

Thus, for determining altered mitochondrial function that is manifest as a cellular response to elevated intracellular calcium, compounds that induce increased cytoplasmic and mitochondrial concentrations of $Ca^{2+}$, including calcium ionophores, are well known to those of ordinary skill in the art, as are methods for measuring intracellular calcium (see, e.g., Gunter and Gunter, *J. Bioenerg. Biomembr.* 26:471, 1994; Gunter et al., *Biochim. Biophys. Acta* 1366:5, 1998; McCormack et al., *Biochim. Biophys. Acta* 973:420, 1989; Orrenius and Nicotera, *J. Neural. Transm. Suppl.* 43:1, 1994; Leist and Nicotera, *Rev. Physiol. Biochem. Pharmacol.* 132:79, 1998; and Haugland, 1996, *Handbook of Fluorescent Probes and Research Chemicals—Sixth Ed.*, Molecular Probes, Eugene, Oreg.). Accordingly, a person skilled in the art may readily select a suitable ionophore (or another compound that results in increased cytoplasmic and/or mitochondrial concentrations of $Ca^{2+}$) and an appropriate means for detecting intracellular calcium for use in identifying altered mitochondrial function, according to the instant disclosure and to well known methods.

$Ca^{2+}$ influx into mitochondria appears to be largely dependent, and may be completely dependent, upon the negative transmembrane electrochemical potential ($\Delta\Psi$) established at the inner mitochondrial membrane by electron transfer, and such influx fails to occur in the absence of $\Delta\Psi$ even when an eight-fold $Ca^{2+}$ concentration gradient is imposed (Kapus et al., 1991 *FEBS Lett.* 282:61). Accordingly, mitochondria may release $Ca^{2+}$ when the membrane potential is dissipated, as occurs with uncouplers like 2,4-dinitrophenol and carbonyl cyanide p-trifluoro-methoxyphenylhydrazone (FCCP). Thus, according to certain embodiments of the present invention, collapse of $\Delta\Psi$ may be potentiated by influxes of cytosolic free calcium into the mitochondria, as may occur under certain physiological conditions including those encountered by cells of a subject having an arthritic disorder. Detection of such collapse may be accomplished by a variety of means as provided herein.

In certain related embodiments of the invention, altered (e.g., increased or decreased in a statistically significant manner relative to a control) mitochondrial membrane potential may be an indicator of altered mitochondrial function. Typically, mitochondrial membrane potential may be determined according to methods with which those skilled in the art will be readily familiar, including but not limited to detection and/or measurement of detectable compounds such as fluorescent indicators, optical probes and/or sensitive pH and ion-selective electrodes (see, e.g., Ernster et al., *J. Cell Biol.* 91:227s, 1981; and references cited; see also Haugland, 1996 *Handbook of Fluorescent Probes and Research Chemicals—Sixth Ed.*, Molecular Probes, Eugene, Oreg., pp. 266–274 and 589–594.). For example, by way of illustration and not limitation, the fluorescent probes 2-,4-dimethylaminostyryl-N-methylpyridinium (DASPMI) and tetramethylrhodamine esters (such as, e.g., tetramethylrhodamine methyl ester, TMRM; tetramethylrhodamine ethyl ester, TMRE) or related compounds (see, e.g., Haugland, 1996, supra) may be quantified following accumulation in mitochondria, a process that is dependent on, and proportional to, mitochondrial membrane potential (see, e.g., Murphy et al., 1998 in *Mitochondria & Free Radicals in Neurodegenerative Diseases*, Beal, Howell and Bodis-Wollner, Eds., Wiley-Liss, New York, pp. 159–186 and references cited therein; and *Molecular Probes On-line Handbook of Fluorescent Probes and Research Chemicals*, at http://www.probes.com/handbook/toc.html). Other fluorescent detectable compounds that may be used in the invention include but are not limited to rhodamine 123, rhodamine B hexyl ester, $DiOC_6(3)$, JC-1 [5,5',6,6'-Tetrachloro-1,1',3,3'-Tetraethylbenzimidazol-carbocyanine Iodide] (see Cossarizza, et al., *Biochem. Biophys. Res. Comm.* 197:40, 1993; Reers et al., *Meth. Enzymol.* 260:406, 1995), rhod-2 (see U.S. Pat. No. 5,049,673; all of the preceding compounds are available from Molecular Probes, Eugene, Oreg.) and rhodamine 800 (Lambda Physik, GmbH, Göttingen, Germany; see Sakanoue et al., *J. Biochem.* 121: 29, 1997). Methods for monitoring mitochondrial membrane potential are also disclosed in U.S. application Ser. No. 09/161,172.

Mitochondrial membrane potential can also be measured by non-fluorescent means, for example by using TTP (tetraphenylphosphonium ion) and a TTP-sensitive electrode (Kamo et al., *J. Membrane Biol.* 49:105, 1979; Porter and Brand, *Am. J. Physiol.* 269:R1213, 1995). Those skilled in the art will be able to select appropriate detectable compounds or other appropriate means for measuring $\Delta\Psi m$. By way of example and not limitation, TMRM is somewhat preferable to TMRE because, following efflux from mitochondria, TMRE yields slightly more residual signal in the endoplasmic reticulicum and cytoplasm than TMRM.

As another non-limiting example, membrane potential may be additionally or alternatively calculated from indirect measurements of mitochondrial permeability to detectable charged solutes, using matrix volume and/or pyridine nucleotide redox determination combined with spectrophotometric or fluorimetric quantification. Measurement of membrane potential dependent substrate exchange-diffusion across the inner mitochondrial membrane may also provide an indirect measurement of membrane potential. (See, e.g., Quinn, 1976, *The Molecular Biology of Cell Membranes*, University Park Press, Baltimore, Md., pp. 200–217 and references cited therein.)

Exquisite sensitivity to extraordinary mitochondrial accumulations of $Ca^{2+}$ that result from elevation of intracellular calcium, as described above, may also characterize a disease associated with altered mitochondrial function. Additionally, a variety of physiologically pertinent agents, including hydroperoxide and free radicals, may synergize with $Ca^{2+}$ to induce collapse of $\Delta\Psi$ (Novgorodov et al., *Biochem. Biophys. Acta* 1058:242, 1991; Takeyama et al., *Biochem. J.* 294:719, 1993; Guidox et al., *Arch. Biochem. Biophys.* 306:139, 1993). Accordingly, non-limiting examples of methods for determining altered mitochondrial function that is manifested in cellular responses to elevated intracellular calcium, or as altered mitochondrial membrane potential, include mitochondrial membrane potential ($\Delta\Psi m$) assays (described in copending U.S. patent application Ser. No. 60/140,433) and mitochondrial permeability transition (MPT) assays (described in copending U.S. patent application Ser. No. 09/161,172).

Altered mitochondrial function may also be determined by comparing a cellular response to an apoptosis-inducing ("apoptogenic") stimulus in a biological sample from (i) a subject believed to be at risk for a disease associated with altered mitochondrial function, and (ii) a control subject. The range of cellular responses to various known apoptogenic stimuli is broad, as is the range of methods and reagents for the detection of such responses. It is therefore within the contemplation of the present invention to determine a disease associated with altered mitochondrial function by so comparing a cellular response to an apoptogenic stimulus, where such response is an indicator of altered mitochondrial function as provided herein.

As noted above, mitochondrial dysfunction and/or related elevated ROS levels may initiate early events leading to apoptosis in various cell types (Kroemer et al., *FASEB J.* 9:1277–87, 1995; Zamzami et al., *J. Exp. Med* 182:367–77, 1995; Zamzami et al., *J. Exp. Med.* 181:1661–72, 1995; Ausserer et al., *Mol. Cell. Biol.* 14:5032–42, 1994). In several cell types, reduction in the mitochondrial membrane potential ($\Delta\Psi m$) precedes the nuclear DNA degradation that accompanies apoptosis. In cell-free systems, mitochondrial, but not nuclear, enriched fractions are capable of inducing nuclear apoptosis (Newmeyer et al., *Cell* 70:353–64, 1994). Perturbation of mitochondrial respiratory activity leading to altered cellular metabolic states, such as elevated intracellular ROS, may occur in a disease associated with altered mitochondrial function and may further induce pathogenetic events via apoptotic mechanisms.

Oxidatively stressed mitochondria may release a preformed soluble factor that can induce chromosomal condensation, an event preceding apoptosis (Marchetti et al., *Cancer Res.* 56:2033–38, 1996). In addition, members of the Bcl-2 family of anti-apoptosis gene products are located within the outer mitochondrial membrane (Monaghan et al., *J. Histochem. Cytochem.* 40:1819–25, 1992) and these proteins appear to protect membranes from oxidative stress (Korsmeyer et al, *Biochim. Biophys. Act.* 1271:63, 1995). Localization of Bcl-2 to this membrane appears to be indispensable for modulation of apoptosis (Nguyen et al., *J. Biol. Chem.* 269:16521–24, 1994). Thus, changes in mitochondrial physiology may be important mediators of apoptosis.

Altered mitochondrial function, as may be used to identify a risk for a disease associated with altered mitochondrial function in a subject according to the present disclosure, may therefore lower the threshold for induction of apoptosis by an apoptogen. A variety of apoptogens are known to those familiar with the art (see, e.g., Green et al., *Science* 281: 1309, 1998; and references cited therein) and may include by way of illustration and not limitation apoptogens that, when added to cells under appropriate conditions with which those skilled in the art will be familiar, require specific receptors such as the tumor necrosis factor, FasL, glutamate, NMDA, IL-1, IL-3, corticosterone, mineralcorticoid or glucocorticoid receptor(s). Apoptogens may further include herbimycin A (Mancini et al., *J. Cell. Biol.* 138:449–69, 1997); paraquat (Costantini et al., *Toxicology* 99:1–2, 1995); ethylene glycols; protein kinase inhibitors such as, e.g.: staurosporine, calphostin C, caffeic acid phenethyl ester, chelerythrine chloride, genistein; 1-(5-isoquinolinesulfonyl)-2-methylpiperazine; N-[2-((p-bromocinnamyl)amino) ethyl]-5-5-isoquinolinesulfonamide; KN-93; quercitin; d-erythro-sphingosine derivatives; UV radiation; ionophores such as, e.g., ionomycin, valinomycin and other ionophores known in the art; MAP kinase inducers such as, e.g., anisomycin and anandamine; cell cycle blockers such as, e.g., aphidicolin, colcemid, 5-fluorouracil and homoharringtonine; acetylcholineesterase inhibitors such as, e.g., berberine; anti-estrogens such as, e.g., tamoxifen; pro-oxidants, such as, e.g., tert-butyl hydroperoxide, peroxynitrite, hydrogen peroxide and nitric oxide donors including but not limited to L-arginine, 5,5'-dinitrosodithiol, N-hydroxy-L-arginine, S-nitroso-N-acetylpenicillamine, S-nitrosoglutathione, NOR-1, NOR-3, NOR4, 4-phenyl-3-furoxancarbonitrile, 3-morpholinosydnonimine, sodium nitroprusside and streptozotocin; glutathione depleting agents such as, e.g., ethacrynic acid (Meister, *Biochim. Biophys. Acta.* 1271:35, 1995); free radicals such as, e.g., nitric oxide; inorganic metal ions, such as, e.g., cadmium; DNA synthesis inhibitors such as, e.g., actinomycin D; DNA intercalators such as, e.g., doxorubicin, bleomycin sulfate, hydroxyurea, methotrexate, mitomycin C, camptothecin, and daunorubicin; protein synthesis inhibitors such as, e.g., cycloheximide, puromycin, and rapamycin; agents that effect microtubule formation or stability such as, e.g.: vinblastine, vincristine, colchicine, 4-hydroxyphenylretinamide, and paclitaxel; and other MPT inducers such as, e.g., Bax protein (Jurgenmeier et al., *PNAS* 95:4997–5002, 1998), calcium and inorganic phosphate (Kroemer et al., *Ann. Rev. Physiol.* 60:619, 1998).

Cells in a biological sample that are suspected of undergoing apoptosis may be examined for morphological, permeability or other changes that are indicative of an apoptotic state. For example by way of illustration and not limitation, apoptosis in many cell types may cause altered morphological appearance such as plasma membrane blebbing, cell shape change, loss of substrate adhesion properties or other morphological changes that can be readily detected by a person having ordinary skill in the art, for example by using light microscopy. As another example, cells undergoing apoptosis may exhibit fragmentation and disintegration of chromosomes, which may be apparent by microscopy and/or through the use of DNA-specific or chromatin-specific dyes that are known in the art, including fluorescent dyes. Such cells may also exhibit altered plasma membrane permeability properties as may be readily detected through the use of vital dyes (e.g., propidium iodide, trypan blue) or by the detection of lactate dehydrogenase leakage into the extracellular milieu. These and other means for detecting apoptotic cells by morphologic criteria, altered plasma membrane permeability and related changes will be apparent to those familiar with the art.

Alternatively, where the indicator of altered mitochondrial function is a cellular response to an apoptogen, cells in a biological sample may be assayed for translocation of cell membrane phosphatidylserine (PS) from the inner to the outer leaflet of the plasma membrane, which may be detected, for example, by measuring outer leaflet binding by the PS-specific protein annexin. (Martin et al., *J. Exp. Med.* 182:1545, 1995; Fadok et al., *J. Immunol.* 148:2207, 1992.) In still another method for determining altered mitochondrial function by monitoring a cellular response to an apoptogen, the cellular response to the apoptogen is determined by an assay for induction of specific protease activity in any member of a family of apoptosis-activated proteases known as the caspases (see, e.g., Green et al., *Science* 281:1309, 1998). Those having ordinary skill in the art will be readily familiar with methods for determining caspase activity, for example by determination of caspase-mediated cleavage of specifically recognized protein substrates. These substrates may include, for example, poly-(ADP-ribose) polymerase (PARP) or other naturally occurring or synthetic peptides and proteins cleaved by caspases that are known in the art (see, e.g., Ellerby et al., *J. Neurosci.* 17:6165, 1997). The synthetic peptide Z-Tyr-Val-Ala-Asp-AFC (SEQ ID. NO:__;), wherein "Z" indicates a benzoyl carbonyl moiety and AFC indicates 7-amino-4-trifluoromethylcoumarin (Kluck et al., *Science* 275:1132, 1997; Nicholson et al., *Nature* 376:37, 1995), is one such substrate. Other non-limiting examples of substrates include nuclear proteins such as U1-70 kDa and DNA-PKcs (Rosen and Casciola-Rosen, *J. Cell. Biochem.* 64:50, 1997; Cohen, Biochem. J. 326:1, 1997).

As described above, the mitochondrial inner membrane may exhibit highly selective and regulated permeability for many small solutes, but is impermeable to large (>~10 kDa) molecules. (See, e.g., Quinn, 1976 *The Molecular Biology of Cell Membranes*, University Park Press, Baltimore, Md.). In cells undergoing apoptosis, however, collapse of mitochondrial membrane potential may be accompanied by increased permeability permitting macromolecule diffusion across the mitochondrial membrane. Thus, in another method for assaying a cellular response to an apoptogen, detection of a mitochondrial protein, for example cytochrome c or an intermembrane space protein, that has escaped from mitochondria in apoptotic cells may provide evidence of a response to an apoptogen that can be readily determined. (Liu et al., *Cell* 86:147, 1996.) Such detection of cytochrome c may be performed spectrophotometrically, immunochemically or by other well established methods for determining the presence of a specific protein.

For instance, release of cytochrome c from cells challenged with apoptotic stimuli (e.g., ionomycin, a well known calcium ionophore) can be followed by a variety of immunological methods. Matrix-assisted laser desorption ionization time-of-flight (MALDI-TOF) mass spectrometry coupled with affinity capture is particularly suitable for such analysis since apo-cytochrome c and holo-cytochrome c can be distinguished on the basis of their unique molecular weights. For example, the Surface-Enhanced Laser Desorption/Ionization (SELDI™) system (Ciphergen, Palo Alto, Calif.) may be utilized to detect cytochrome c release from mitochondria in apoptogen treated cells. In this approach, a cytochrome c specific antibody immobilized on a solid support is used to capture released cytochrome c present in a soluble cell extract. The captured protein is then encased in a matrix of an energy absorption molecule (EAM) and is desorbed from the solid support surface using pulsed laser excitation. The molecular mass of the protein is determined by its time of flight to the detector of the SELDI™ mass spectrometer.

A person having ordinary skill in the art will readily appreciate that there may be other suitable techniques for quantifying apoptosis, and such techniques for purposes of determining altered mitochondrial function as manifested in a cellular response to an apoptogenic stimulus are within the scope of the methods provided by the present invention.

Detection of free radical production in a biological sample may also be employed to determine the presence of altered mitochondrial function, in a biological sample from a subject. Although mitochondria are a primary source of free radicals in biological systems (see, e.g., Murphy et al., 1998 in *Mitochondria and Free Radicals in Neurodegenerative Diseases*, Beal, Howell and Bodis-Wollner, Eds., Wiley-Liss, New York, pp. 159–186 and references cited therein), the invention should not be so limited and free radical production can be an indicator of altered mitochondrial function regardless of the particular subcellular source site. For example, numerous intracellular biochemical pathways that lead to the formation of radicals through production of metabolites such as hydrogen peroxide, nitric oxide or superoxide radical via reactions catalyzed by enzymes such as flavin-linked oxidases, superoxide dismutase or nitric oxide synthetase, are known in the art, as are methods for detecting such radicals (see, e.g., Kelver, *Crit. Rev. Toxicol.* 23:21, 1993; Halliwell B. et al., *Free Radicals in Biology and Medicine,* 1989, Clarendon Press, Oxford, UK; Davies, K. J. A. et al., *The Oxygen Paradox*, Cleup Univ. Press, Padova, IT). Altered mitochondrial function, such as failure at any step of the ETC, may also lead to the generation of highly reactive free radicals. As noted above, radicals resulting from altered mitochondrial function include reactive oxygen species (ROS), for example, superoxide, peroxynitrite and hydroxyl radicals, and potentially other reactive species that may be toxic to cells. Accordingly, in certain preferred embodiments of the invention an indicator of altered mitochondrial function may be a detectable free radical species present in a biological sample. In certain particularly preferred embodiments, the detectable free radical will be a ROS.

Methods for detecting a free radical that may be useful as an indicator of altered mitochondrial function are known in the art and will depend on the particular radical. Typically, a level of free radical production in a biological sample may be determined according to methods with which those skilled in the art will be readily familiar, including but not limited to detection and/or measurement of: glycoxidation products including pentosidine, carboxymethylysine and pyrroline; lipoxidation products including glyoxal, malondialdehyde and 4-hydroxynonenal; thiobarbituric acid reactive substances (TBARS; see, e.g., Steinbrecher et al., *Proc. Nat. Acad. Sci. USA* 81:3883, 1984; Wolff, *Br. Med. Bull.* 49:642, 1993) and/or other chemical detection means such as salicylate trapping of hydroxyl radicals (e.g., Ghiselli et al., *Meths. Mol. Biol.* 108:89, 1998; Halliwell et al., *Free Radic. Res.* 27:239, 1997) or specific adduct formation (see, e.g., Mecocci et al., *Ann. Neurol.* 34:609, 1993; Giulivi et al., *Meths. Enzymol.* 233:363, 1994) including malondialdehyde formation, protein nitrosylation, DNA oxidation including mitochondrial DNA oxidation, 8'-OH-guanosine adducts (e.g., Beckman et al., *Mutat. Res.* 424:51, 1999), protein oxidation, protein carbonyl modification (e.g., Baynes et al., *Diabetes* 40:405, 1991; Baynes et al., *Diabetes* 48:1, 1999); electron spin resonance (ESR) probes; cyclic voltametry; fluorescent and/or chemiluminescent indicators (see also e.g., Greenwald, R. A. (ed.), *Handbook of Methods for Oxygen Radical Research,* 1985, CRC Press, Boca Raton, Fla.; Acworth and Bailey, (eds.), *Handbook of Oxidative Metabolism,* 1995, ESA, Inc., Chelmsford, Mass.; Yla-Herttuala et al., *J. Clin. Invest.* 84:1086, 1989; Velazques et al., *Diabetic Medicine* 8:752, 1991; Belch et al., *Int. Angiol.* 14:385, 1995; Sato et al., *Biochem. Med.* 21:104, 1979; Traverso et al., *Diabetologia* 41:265, 1998; Haugland, 1996 *Handbook of Fluorescent Probes and Research Chemicals—Sixth Ed.*, Molecular Probes, Eugene, Oreg., pp. 483–502, and references cited therein). For example, by way of illustration and not limitation, oxidation of the fluorescent probes dichlorodihydrofluorescein diacetate and its carboxylated derivative carboxydichlorodihydrofluorescein diacetate (see, e.g., Haugland, 1996, supra) may be quantified following accumulation in cells, a process that is dependent on, and proportional to, the presence of reactive oxygen species (see also, e.g., *Molecular Probes On-line Handbook of Fluorescent Probes and Research Chemicals*, at http://www.probes.com/handbook/toc.html). Other fluorescent detectable compounds that may be used in the invention for detection of free radical production include but are not limited to dihydrorhodamine and dihydrorosamine derivatives, cis-parinaric acid, resorufin derivatives, lucigenin and any other suitable compound that may be known to those familiar with the art.

Thus, as also described above, free radical mediated damage may inactivate one or more of the myriad proteins of the ETC and in doing so, may uncouple the mitochondrial chemiosmotic mechanism responsible for oxidative phosphorylation and ATP production. Indicators of altered mitochondrial function that are ATP biosynthesis factors, including determination of ATP production, are described in greater detail, for example, in PCT/US00/25317 and in U.S. Pat. No. 6,140,067. Free radical mediated damage to mitochondrial functional integrity is also just one example of multiple mechanisms associated with altered mitochondrial function that may result in collapse of the electrochemical potential maintained by the inner mitochondrial membrane. Methods for detecting changes in the inner mitochondrial membrane potential are described above and in co-pending U.S. patent application Ser. No. 09/161,172.

Biological samples may comprise any tissue or cell preparation in which at least one candidate indicator of altered mitochondrial function can be detected, and may vary in nature accordingly, depending on the particular indicator(s) to be compared. Thus, as will be apparent to those having ordinary skill in the art based on the disclosure herein, in certain highly preferred embodiments biological samples comprise cells or cell preparations containing mitochondria, and in certain other preferred embodiments biological samples may comprise submitochondrial particles. Biological samples may be provided by obtaining a blood sample, biopsy specimen, tissue explant, organ culture or any other tissue or cell preparation from a subject or a biological source. The subject or biological source may be a human or non-human animal, a primary cell culture or culture adapted cell line including but not limited to genetically engineered cell lines that may contain chromosomally integrated or episomal recombinant nucleic acid sequences, immortalized or immortalizable cell lines, somatic cell hybrid or cytoplasmic hybrid "cybrid" cell lines, differentiated or differentiatable cell lines, transformed cell lines and the like. In particularly preferred embodiments the subject or biological source is a human or non-human vertebrate, and in other particularly preferred embodiments the subject or biological source is a vertebrate-derived primary cell culture or culture-adapted cell line as provided herein, but the invention need not be so limited. As a non-limiting example by way of illustration, in certain embodiments the invention contemplates a biological sample that may be a non-vertebrate tissue or cell preparation that has been artificially manipulated, for example through recombinant genetic engineering, to contain one or more vertebrate-derived genes, gene products or the like, such as mitochondrial molecular components and/or ATP biosynthesis factors as provided, for example, in PCT/US00/25317 and in U.S. Pat. No. 6,140,067. For instance, a number of yeast and insect cell lines may be readily reconstituted with heterologous vertebrate-derived components according to established methods with which those skilled in the art will be familiar, to generate a model system for a disease associated with altered mitochondrial function as provided herein. Accordingly, numerous variations and modifications to biological samples are within the contemplated scope and spirit of the present invention.

In certain other particularly preferred embodiments of the invention, the subject or biological source may be suspected of having or being at risk for having an arthritic disorder and/or a disease associated with altered mitochondrial function, and in certain preferred embodiments of the invention the subject or biological source may be known to be free of a risk or presence of such a disease. In certain other preferred embodiments where it is desirable to determine whether or not a subject or biological source falls within clinical parameters indicative of an arthritic disorder, signs and symptoms of an arthritic disorder that are accepted by those skilled in the art may be used to so designate a subject or biological source, for example clinical signs referred to in *Primer on the Rheumatic Diseases* (7*th* Edition, J. H. Klippel (ed.), 1997 The Arthritis Foundation, Atlanta, Ga.) and references cited therein, or other means known in the art for diagnosing an arthritic disorder. Similarly, clinical parameters indicative of certain other diseases associated with altered mitochondrial function as provided herein are known to the art and are discussed above.

In certain embodiments of the invention, biological samples from a subject or biological source in which at least one altered mitochondrial function has been detected may be compared before and after contacting the subject or biological source with a composition of structure (I) such as an aryl N-cyanoguanidine agent as provided herein, for example to identify a candidate mitochondrial function in which the agent is capable of effecting a change, relative to the level of the mitochondrial function before exposure of the subject or biological source to the agent.

In a most preferred embodiment of the invention, the biological sample containing in which altered mitochondrial function is determined comprises a chondrocyte, and still more preferably, an articular chondrocyte. Chondrocytes can be obtained, for example, from normal mature cartilage tissue. For instance, U.S. Pat. Nos. 4,846,835 and 5,041,138 disclose isolation of chondrocytes by digesting articular cartilage in a collagenase solution, followed by mitotic expansion of the chondrocytes in vitro. In another preferred embodiment of the invention, the biological sample containing at least one candidate indicator of altered mitochondrial function may comprise a matrix vesicle (MV) derived from a chondrocyte (e.g., Anderson, *Rheum. Dis. Clin. North Amer.* 14:303, 1988; Doyle, *J. Pathol.* 136:199, 1982; Doherty, *Hosp. Pract. Off. Ed.* 29:93, 1994), for example, an MV prepared according to any of a number of established procedures (e.g., Johnson et al., *J. Bone Miner. Res.* 14:883, 1999) or by other techniques with which those having ordinary skill in the art will be familiar.

The initiation of matrix calcification by chondrocytes, as well as by osteoblasts, appears to be mediated by the release of membrane-limited cell fragments known as matrix vesicles (MVs). MV components, including a variety of enzymes, modify the extracellular matrix, and the MV interiors serve as a sheltered environment for hydroxyapatite crystal formation (Anderson, *Clin. Orthopaed Rel. Res.* 314:266–80, 1995; Boskey et al., *Calcif. Tissue Int.* 60:309–15, 1997; Boskey, *Connect. Tissue Res.* 35:357–63, 1996; and Goldberg, *Prog. Histochem. Cytochem.* 31: 1–187, 1996). Methods of preparing MVs are described herein, and other methods are known in the art (see, e.g., Johnson et al., *J. Bone Miner. Res.* 14:883–92, 1999, and U.S. Pat. No. 5,656,450).

Mitochondria and SMPs can be prepared by a variety of methods (see, e.g., Fleischer et al., *Methods Enzymol.* 31:292–99, 1974; Pedersen et al., *Methods Cell. Biol.* 20:411–81, 1978; della-Cioppa et al., *Mol. Cell. Endocrinol.* 48:111–20, 1986; and Lauquin et al., *Biochim. Biophys. Acta* 460:331–45, 1977). For example, to prepare mitochondria and/or SMPs, the following procedure may be used. Cell lysates are centrifuged at 600×g for 10 minutes at 4° C., and this first supernatant is removed and set aside. The pellet, which comprises plasma membrane material, is washed with 100 µl of MSB (210 mM mannitol, 70 mM sucrose, 50 mM Tris-HCl, pH 7.4, and 10 mM EDTA) and centrifuged at 600×g for 10 minutes at 4° C., in order to produce a second supernatant. The first and second supernatants are combined and centrifuged at 14,000×g for 15 minutes at 4° C.; the resultant pellet represents a mitochondrial fraction that is resuspended in MSB in order to prepare mitochondria. Such mitochondria may be incubated with 0.25 mg/ml digitonin (Roche Molecular Biochemicals, Indianapolis, Ind.) for 2 minutes and sonicated for 3 minutes at 50% duty cycle in a cup-horn sonicator to produce submitochondrial particles (SMPs).

Accordingly, a biological sample as provided herein may in certain preferred embodiments comprise a chondrocyte, chondrocyte-derived MVs and/or chondrocyte-derived submitochondrial particles (SMP), in which levels of one or more indicators of altered mitochondrial function may be compared.

In another preferred embodiment of the invention, the biological sample containing at least one candidate indicator of altered mitochondrial function may comprise whole blood, and may in another preferred embodiment comprise a crude buffy coat fraction of whole blood, which is known in the art to comprise further a particulate fraction of whole blood enriched in platelets and in nucleated blood cells (e.g., white blood cells such as lymphocytes, monocytes and granulocytes including neutrophils, eosinophils and basophils), and substantially depleted of erythrocytes. Those familiar with the art will know how to prepare such a buffy coat fraction, which may be prepared, for example, by differential density sedimentation of blood components under defined conditions, including the use of density dependent separation media, or by other methods. In other preferred embodiments, the biological sample containing at least one indicator of altered mitochondrial function may comprise an enriched, isolated or purified blood cell subpopulation fraction such as, for example, lymphocytes, polymorphonuclear leukocytes, granulocytes and the like. Methods for the selective preparation of particular hematopoietic cell subpopulations are well known in the art (see, e.g., *Current Protocols in Immunology*, J. E. Coligan et al., (Eds.) 1998, John Wiley & Sons, NY).

According to certain embodiments of the invention, the particular cell type or tissue type from which a biological sample is obtained may influence qualitative or quantitative aspects of at least one candidate indicator of altered mitochondrial function contained therein, relative to the corresponding candidate indicator of altered mitochondrial function obtained from distinct cell or tissue types of a common biological source. It is therefore within the contemplation of the invention to quantify at least one candidate indicator of altered mitochondrial function in biological samples from different cell or tissue types as may render the advantages of the invention most useful for a particular indication, for example, an arthritic disorder or a disease associated with altered mitochondrial function as provided herein, and further for a particular degree of progression of a known or suspected arthritic disorder (or disease associated with altered mitochondrial function) in a vertebrate subject. The relevant cell or tissue types will be known to those familiar with such diseases.

For example, as provided herein, articular cartilage chondrocytes may represent a particularly preferred cell type in the context of an arthritic disorder, as also may other cell types in joint development, stabilization, maintenance and repair processes such as cartilage homeostasis, bone or ligament graft healing, scar tissue resorption or connective tissue remodeling, for example, bone cells, osteoblasts, osteoclasts, bone marrow stromal cells, myocytes, motor nerve/end plate cells, inflammatory cells and/or synoviocytes.

In order to determine whether a mitochondrial alteration may contribute to a particular disease state, it may be useful to construct a model system for diagnostic tests and for screening candidate therapeutic agents in which the nuclear genetic background may be held constant while the mitochondrial genome is modified. It is known in the art to deplete mitochondrial DNA from cultured cells to produce $\rho^0$ cells, thereby preventing expression and replication of mitochondrial genes and inactivating mitochondrial function. It is further known in the art to repopulate such $\rho^0$ cells with mitochondria derived from foreign cells in order to assess the contribution of the donor mitochondrial genotype to the respiratory phenotype of the recipient cells. Such cytoplasmic hybrid cells, containing genomic and mitochondrial DNAs of differing biological origins, are known as cybrids. See, for example, International Publication Number WO 95/26973 and U.S. Pat. No. 5,888,498 which are hereby incorporated by reference in their entireties, and references cited therein.

In certain other embodiments, the invention provides a method of treating a patient having an arthritic disorder by administering to the patient a composition comprising an agent having chemical structure (I) that substantially improves (e.g., alters to be closer to a control or asymptomatic state in a statistically significant manner) at least one clinical criterion for having or being at risk for having an arthritic disorder (see, e.g., *Primer on the Rheumatic Diseases*, 7$^{th}$ Edition, J. H. Klippel (ed.), 1997 The Arthritis Foundation, Atlanta, Ga.). The invention also provides a method of treating a patient having a disease associated with altered mitochondrial function by administering to the patient a composition comprising an agent having chemical structure (I) that substantially improves (e.g., alters to be closer to a control or asymptomatic state in a statistically significant manner) at least one clinical criterion for having or being at risk for having such a disease, as known in the art and as provided herein. Those having ordinary skill in the art can readily determine whether a change in such clinical criterion brings that level closer to a normal value and/or clinically benefits the subject. Thus, a preferred agent provided by the present invention may include an agent capable of fully or partially restoring such level.

Accordingly, in certain preferred embodiments as provided herein, a pharmaceutical composition suitable for treating an arthritic disorder and/or for treating a disease associated with altered mitochondrial function comprises an agent of structure (I), e.g., an aryl N-cyanoguanidine agent. In the case of arthritic disorders, such agents may be used to prevent or treat arthritic disorders, such as osteoarthritis, degenerative joint disease and the like, and to promote the healing of injured cartilage, for example, cartilage damaged by trauma or repetitive motion disorder. Without wishing to be bound by any particular theory, some such agents may have activity as antioxidants and presumably act by preventing or ameriolating the effects of oxidative stress damage to mitochondria (for a review, see, e.g., Kowaltowski et al., *Free Radical Biol. Med.* 26:463–471, 1999). These and/or other such agents may act to prevent programmed cell death (apoptosis), which may contribute to the development of osteoarthritis (Blanco et al., *Arthritis & Rheumatism* 41:284–289, 1998) and/or to other diseases associated with altered mitochondrial function as provided herein, or may exert clinically beneficial effects through other mechanisms.

Thus, within these and other related embodiments, a composition comprising structure (I) (e.g., an aryl N-cyanoguanidine agent) such as those provided herein may be administered to a patient for treatment or prevention of an arthritic disorder or a disease associated with altered mitochondrial function as provided herein. In certain preferred embodiments the agent is therefore a mitochondrial function-altering agent. Therapeutic agents provided herein are preferably part of a pharmaceutical composition when used in the methods of the present invention. The pharmaceutical composition will include at least one of a pharmaceutically acceptable carrier, diluent or excipient, in addition to one or more mitochondrial function-altering agents and, optionally, other components.

A compound according to this invention (e.g., a composition of structure (I) such as an aryl N-cyanoguanidine agent), or a pharmaceutically acceptable salt thereof, is administered to a patient in a therapeutically effective amount. A therapeutically effective amount is an amount calculated to achieve the desired effect. It will be apparent to one skilled in the art that the route of administration may vary with the particular treatment. Routes of administration may be either non-invasive or invasive. Non-invasive routes of administration include oral, buccal/sublingual, rectal, nasal, topical (including transdermal and ophthalmic), vaginal, intravesical, and pulmonary. Invasive routes of administration include intraarterial, intravenous, intradermal, intramuscular, subcutaneous, intraperitoneal, intrathecal and intraocular.

The required dosage may vary with the particular treatment and route of administration. In general, dosages for compounds of this invention such as aryl N-cyanoguanidine agents of structure (I) as described herein will be from about 1 to about 5 milligrams of the compound per kilogram of the body weight of the host animal per day; frequently it will be between about 100 μg and about 5 mg but may vary up to about 50 mg of compound per kg of body weight per day. Therapeutic administration is generally performed under the guidance of a physician, and pharmaceutical compositions contain the agent in a pharmaceutically acceptable carrier. These carriers are well known in the art and typically contain non-toxic salts and buffers. Such carriers may comprise buffers like physiologically-buffered saline, phosphate-buffered saline, carbohydrates such as glucose, mannose, sucrose, mannitol or dextrans, amino acids such as glycine, antioxidants, chelating agents such as EDTA or glutathione, adjuvants and preservatives. Acceptable nontoxic salts include acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

In one embodiment of the invention, pharmaceutical compositions comprising one or more compounds of this invention are entrapped within liposomes. Liposomes are microscopic spheres having an aqueous core surrounded by one or more outer layer(s) made up of lipids arranged in a bilayer configuration (see, e.g., Chonn et al., *Current Op. Biotech.* 6:698, 1995). The therapeutic potential of liposomes as drug delivery agents was recognized nearly thirty years ago (Sessa et al., *J. Lipid Res.* 9:310, 1968). Liposomes include "sterically stabilized liposome," a term which, as used herein, refers to a liposome comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome (A) comprises one or more glycolipids, such as monosialoganglioside $G_{M1}$, or (B) is derivatized with one or more hydrophilic polymers, such as a polyethylene glycol (PEG) moiety. While not wishing to be bound by any particular theory, it is thought in the art that, at least for sterically stabilized liposomes containing gangliosides, sphingomyelin, or PEG-derivatized lipids, the enhanced circulation half-life of these sterically stabilized liposomes derives from a reduced uptake into cells of the reticuloendothelial system (RES) (Allen et al., *FEBS Letters* 223:42, 1987; Wu et al., *Cancer Research* 53:3765, 1993).

Various liposomes comprising one or more glycolipids are known in the art. Papahadjpoulos et al. (*Ann. N.Y. Acad. Sci.*, 507:64, 1987) reported the ability of monosialoganglioside $G_{M1}$, galactocerebroside sulfate and phosphatidylinositol to improve blood half-lives of liposomes. These findings were expounded upon by Gabizon et al. (*Proc. Natl. Acad. Sci. U.S.* 85:6949, 1988). U.S. Pat. No. 4,837,028 and WO 88/04924, both to Allen et al., disclose liposomes comprising (1) sphingomyelin and (2) the ganglioside $G_{M1}$ or a galactocerebroside sulfate ester. U.S. Pat. No. 5,543,152 (Webb et al.) discloses liposomes comprising sphingomyelin. Liposomes comprising 1,2-sn-dimyristoylphosphatidylcholine are disclosed in WO 97/13499 (Lim et al.).

Various liposomes comprising lipids derivatized with one or more hydrophilic polymers, and methods of preparation thereof, are known in the art. Sunamoto et al. (*Bull. Chem. Soc. Jpn.* 53:2778, 1980) described liposomes comprising a nonionic detergent, $2C_{12}15G$, that contains a PEG moiety. Illum et al. (*FEBS Letters* 167:79, 1984) noted that hydrophilic coating of polystyrene particles with polymeric glycols results in significantly enhanced blood half-lives. Synthetic phospholipids modified by the attachment of carboxylic groups of polyalkylene glycols (e.g., PEG) are described by Sears (U.S. Pat. Nos. 4,426,330 and 4,534,899). Klibanov et al. (*FEBS Letts.* 268:235, 1990) described experiments demonstrating that liposomes comprising phosphatidylethanolamine (PE) derivatized with PEG or PEG stearate have significant increases in blood circulation half-lives. Blume et al. (*Biochimica et Biophysica Acta* 1029:91, 1990) extended such observations to other PEG-derivatized phospholipids, e.g., DSPE-PEG, formed from the combination of distearoylphosphatidylethanolamine (DSPE) and PEG. Liposomes having covalently bound PEG moieties on their external surface are described in European Patent No. 0 445 131 B1 and WO 90/04384 to Fisher. Liposome compositions containing 1–20 mole percent of PE derivatized with PEG, and methods of use thereof, are described by Woodle et al. (U.S. Pat. Nos. 5,013,556 and 5,356,633) and Martin et al. (U.S. Pat. No. 5,213,804 and European Patent No. EP 0 496 813 B1). Liposomes comprising a number of other lipid-polymer conjugates are disclosed in WO 91/05545 and U.S. Pat. No. 5,225,212 (both to Martin et al.) and in WO 94/20073 (Zalipsky et al.) Liposomes comprising PEG-modified ceramide lipids are described in WO 96/10391 (Choi et al.). U.S. Pat. No. 5,540,935 (Miyazaki et al.) and U.S. Pat. No. 5,556,948 (Tagawa et al.) describe PEG-containing liposomes that can be further derivatized with functional moieties on their surfaces.

Compounds of the present invention (e.g., compositions of structure (I) such as aryl N-cyanoguanidine agents) as provided by the present invention also include prodrugs thereof. As used herein, a "prodrug" is any covalently bonded carrier that releases in vivo the active parent drug when such prodrug is administered to a vertebrate subject. Prodrugs of a given compound are prepared by modifying functional groups present on the compound in such a way that the modifications are cleaved, either in routine manipulation or in vivo, to the parent compound. Prodrugs include, but are not limited to, compounds wherein hydroxy, amine or sulfhydryl groups are bonded to any group of the parent compound via a bond that, when the prodrug is administered to a subject, cleaves to form the free hydroxyl, amino or sulfhydryl group, respectively. Representative examples of prodrugs include, but are not limited to, acetate, formate and benzoate derivatives of alcohol and amine functional groups.

"Pharmaceutically acceptable carriers" for therapeutic use are well known in the pharmaceutical art, and are described, for example, in *Remingtons Pharmaceutical Sciences*, Mack Publishing Co. (A. R. Gennaro edit. 1985). For example, sterile saline and phosphate-buffered saline at physiological pH may be used. Preservatives, stabilizers, dyes and even flavoring agents may be provided in the pharmaceutical composition. For example, sodium benzoate, sorbic acid and esters of p-hydroxybenzoic acid may be added as preservatives. In addition, antioxidants and suspending agents may be used. Optionally, for certain routes of administration, an anesthetic may be included in the formulation.

Pharmaceutically acceptable salts of the compounds of this invention may be made by techniques well known in the art, such as by reacting the free acid or base forms of these compounds with a stoichiometric amount of the appropriate base or acid in water of in an organic solvent. Suitable salts in this context may be found in *Remington's Pharmaceutical Sciences*, 17$^{th}$ ed., Mack Publishing Co., Easton, Pa., 1985, which is hereby incorporated by reference.

By way of example and not limitation, suitable pharmaceutically acceptable salts of the compounds of this invention include acid addition salts which may, for example, be formed by mixing a solution of the compound according to the invention with a solution of an acceptable acid such as hydrobromic acid, hydrochloric acid, fumaric acid, oxalic acid, p-toluenesulphonic acid, malic acid, maleic acid, methanesulfonic acid, succinic acid, acetic acid, citric acid, tartaric acid, carbonic acid, phosphoric acid, sulphuric acid and the like. The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin. By way of example and not limitation, suitable pharmaceutically acceptable salts of the compounds of this invention include acid addition salts which may, for example, be formed by mixing a solution of the compound according to the invention with a solution of an acceptable acid such as hydrobromic acid, hydrochloric acid, fumaric acid, oxalic acid, p-toluenesulphonic acid, malic acid, maleic acid, methanesulfonic acid, succinic acid, acetic acid, citric acid, tartaric acid, carbonic acid, phosphoric acid, sulphuric acid and the like. The salts may be formed by conventional means, such as by reacting the free base form of the product with one or more equivalents of the appropriate acid in a solvent or medium in which the salt is insoluble, or in a solvent such as water which is removed in vacuo or by freeze drying or by exchanging the anions of an existing salt for another anion on a suitable ion exchange resin.

The pharmaceutical compositions that contain one or more compounds of the invention as disclosed herein may be in any form which allows for the composition to be administered to a patient. For example, the composition may be in the form of a solid, liquid or gas (aerosol). Typical routes of administration include, without limitation, oral, topical, parenteral (e.g., sublingually or buccally), sublingual, rectal, vaginal, and intranasal. The term parenteral as used herein includes subcutaneous injections, intravenous, intramuscular, intrasternal, intrathecal, intracavernous, intrameatal, intraurethral injection or infusion techniques.

The pharmaceutical composition is formulated so as to allow the active ingredients contained therein to be bioavailable upon administration of the composition to a patient. Compositions that will be administered to a patient take the form of one or more dosage units, where for example, a tablet may be a single dosage unit, and a container of one or more compounds of the invention in aerosol form may hold a plurality of dosage units.

For oral administration, an excipient and/or binder may be present. Examples are sucrose, kaolin, glycerin, starch dextrins, sodium alginate, carboxymethylcellulose and ethyl cellulose. Coloring and/or flavoring agents may be present. A coating shell may be employed. The composition may be in the form of a liquid, e.g., an elixir, syrup, solution, emulsion or suspension. The liquid may be for oral administration or for delivery by injection, as two examples. When intended for oral administration, preferred compositions contain, in addition to one or more compounds of structure (I), one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

A liquid pharmaceutical composition as used herein, whether in the form of a solution, suspension or other like form, may include one or more of the following adjuvants: sterile diluents such as water for injection, saline solution, preferably physiological saline, Ringer's solution, isotonic sodium chloride, fixed oils such as synthetic mono or digylcerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

A liquid composition intended for either parenteral or oral administration should contain an amount of a compound of structure (I) such that a suitable dosage will be obtained. Typically, this amount is at least 0.01 wt % of a compound of the invention in the composition. When intended for oral administration, this amount may be varied to be between 0.1 and about 70% of the weight of the composition. Preferred oral compositions contain between about 4% and about 50% of the compound of the invention. Preferred compositions and preparations are prepared so that a parenteral dosage unit contains between 0.01 to 1% by weight of active compound.

The pharmaceutical composition may be intended for topical administration, in which case the carrier may suitably comprise a solution, emulsion, ointment or gel base. The base, for example, may comprise one or more of the following: petrolatum, lanolin, polyethylene glycols, beeswax, mineral oil, diluents such as water and alcohol, and emulsifiers and stabilizers. Thickening agents may be present in a pharmaceutical composition for topical administration. If intended for transdermal administration, the composition may include a transdermal patch or iontophoresis device. Topical formulations may contain a concentration of the compound of the invention of from about 0.1 to about 10% w/v (weight per unit volume).

The composition may be intended for rectal administration, in the form, e.g., of a suppository that will melt in the rectum and release the drug. The composition for rectal administration may contain an oleaginous base as a suitable nonirritating excipient. Such bases include, without limitation, lanolin, cocoa butter and polyethylene glycol.

In certain preferred methods of the invention, the compound(s) of the invention may be administered through use of insert(s), bead(s), timed-release formulation(s), patch(es) or fast-release formulation(s). It will be evident to those of ordinary skill in the art that the optimal dosage of the agent(s) may depend on the weight and physical condition of the patient; on the severity and longevity of the physical condition being treated; on the particular form of the active ingredient, the manner of administration and the composition employed. It is to be understood that use of the compounds of the present invention in chemotherapy can involve such an agent being bound to another compound, for example, a monoclonal or polyclonal antibody, a protein or a liposome, which assist the delivery of said compound.

These and related advantages will be appreciated by those familiar with the art. The following Examples are offered by way of illustration and not limitation.

EXAMPLES

Example 1

General Synthesis of Representative Compounds

N-Cyano-S-methylisothiourea (1.38 g, 12.0 mmol) was dissolved in i-PrOH (18.0 mL). To this stirred solution was added aqueous NaOH (2.0 M, 6.0 mL), and the resulting reaction mixture was heated at 100° C. for 30 min. The solution was allowed to cool down to ambient temperature, and 2.0 ml portions (each containing ca 1.0 mmol of the putative intermediate salt, sodium dicyanamide) were added to a solution of the appropriate aniline (1.0 mmol) in $HCl_{(aq)}$ (1.0 M, 1.0 mL). The reaction mixture was heated at 100° C. for 60 min with agitation.

After cooling down to room temperature, the reaction mixture was evaporated under reduced pressure furnishing the crude product of structure (I). Prior to purification, each crude mixture was taken up in MeOH (10 mL), sonicated to break up solids, and filtered through 0.20 micron PTFE membrane filters. Preparative RP-HPLC was performed on an automated Gilson 215 HPLC system, each derivative being purified in three batches (3.3 mL injection volumes) over a Betasil™ C18 column (150×20 mm, 5µ particles, 100 Å pores, Keystone Scientific, Inc., Bellefonte, Pa.). The product was eluted using a gradient of MeCN:TFA (10000:5) in $H_2O$:TFA (10000:5) at a flowrate of 15.0 mL/min. Appropriate fractions were analyzed for presence of desired product by LC/MS. The pooled fractions were concentrated and repeatedly co-evaporated with MeOH (3×5.0 mL). LC/MS and NMR analyses were used for final confirmation of structure. Yields were in the range 10–65%.

The representative compounds made by this procedure, along with corresponding analytical data, are summarized in the following Table 1.

TABLE 1

Representative Compounds

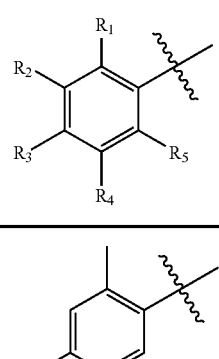

(I)

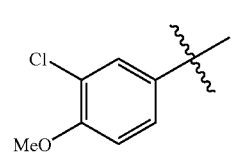

| Cpd. | | ESI-MS [M + H]⁺ (calculated/observed) | ¹H-NMR |
|---|---|---|---|
| (1) | (2-methyl-4-hydroxyphenyl) | 191.1/191.2 | (d₆-DMSO) 9.35(s, 1H), 8.33(s, 1H), 6.94(m, 1H), 6.68(b, 2H), 6.62(s, 1H), 6.56(m, 1H) |
| (2) | (3-chloro-4-methoxyphenyl) | 225.0/225.2 | (d₆-DMSO) 8.97(s, 1H), 7.45(m, 1H), 7.19(m, 1H), 7.09(d, 1H), 6.99(b, 2H), 3.82(s, 3H) |

TABLE 1-continued

Representative Compounds (I)

[Structure: phenyl ring with R1, R2, R3, R4, R5 substituents, bonded via NH to C(=NCN)NH2]

[Aryl substituent template with R1, R2, R3, R4, R5]

| Cpd. | [Aryl group] | ESI-MS [M + H]+ (calculated/observed) | 1H-NMR |
|---|---|---|---|
| (3) | 4-morpholinophenyl | 246.1/246.3 | (d6-DMSO) 8.85(s, 1H), 7.18(m, 2H), 6.92(d, 2H), 6.83(m, 2H), 3.73(dd, 4H), 3.07(dd, 4H) |
| (4) | 3,4,5-trimethoxyphenyl | 251.1/251.2 | (d6-DMSO) 8.99(s, 1H), 6.95(b, 2H), 6.65(s, 2H), 3.73(s, 6H), 3.62(s, 3H) |
| (5) | 3-(trifluoromethyl)phenyl | 229.1/229.2 | (d6-DMSO) 9.37(s, 1H), 7.80(s, 1H), 7.62(d, 1H), 7.53(t, 1H), 7.44(d, 1H) |
| (6) | 2,4-dimethylphenyl | 189.1/189.2 | (CDCl3) 7.19(s, 1H), 7.09(m, 3H), 5.46(b, 2H), 2.38(s, 3H), 2.26(s, 3H) |
| (7) | 3,5-dimethylphenyl | 189.1/189.2 | (CDCl3) 7.53(s, 1H), 6.94(s, 1H), 6.87(s, 2H), 5.68(b, 2H), 2.32(s, 6H) |
| (8) | 4-chloro-2-methylphenyl | 209.1/209.2 | (d6-DMSO) 8.54(s, 1H), 7.31(m, 2H), 7.22(m, 1H), 7.02(b, 2H), 2.17(s, 3H) |

TABLE 1-continued

Representative Compounds

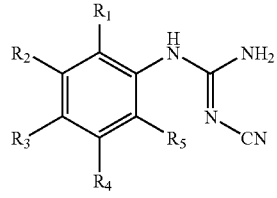

| Cpd. | | ESI-MS [M + H]+ (calculated/observed) | 1H-NMR |
|---|---|---|---|
| (9) | 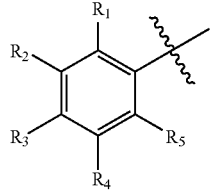 | 289.0/289.2 | (d6-DMSO) 9.22(s, 1H), 8.18(d, 1H), 7.98(d, 1H), 7.88(d, 1H), 7.72(m, 2H), 7.46(m, 1H), 7.14(b, 2H) |

Example 2

Representative Large-Scale Synthesis of Compound (1)

N-Cyano-S-methylisothiourea (576 mg, 5.00 mmol) was dissolved in i-PrOH (7.5 mL). To this stirred solution was added aqueous NaOH (2.0 M, 2.5 mL), and the resulting reaction mixture was heated to 100° C. for 30 min. The solution was allowed to cool down to ambient temperature. To this dicyanamide solution was added a solution of 4-hydroxy-2-methylaniline (616 mg, 5.00 mmol) in HCl$_{(aq)}$ (1.0 M, 5.0 mL). The reaction mixture was heated at 100° C. for 60 min, and after cooling to ambient temperature, evaporated to dryness. To the crude was added an equivalent weight of silica gel and MeOH (10 mL/g crude). After stirring for a few minutes, the MeOH was removed by rotary evaporation, and the silica/crude further freed of MeOH by evaporation of added dichloromethane (DCM, 10 mL/g crude). This coevaporation step was repeated three times. The silica/crude mix was placed on top of a flash-SGC equilibrated with DCM/MeOH (95:5). Elution with a step-wise gradient of MeOH in DCM (5–10%) afforded Compound (1) as a light brown solid after drying under high vacuum. Yield: 482 mg (50.7%).

Example 3

Chondrocyte Activity Assay

Immortalized TC28 (a.k.a. "T/C-28") juvenile rib chondrocytes were provided by Dr. Mary Goldring (Harvard Medical School, Boston, Mass.). The TC28 cells were maintained in monolayer culture in DMEM/Ham's F12 (1:1) and supplemented with 10% FCS, 1% L-glutamine, 100 units/ml Penicillin and 50 mg/ml Streptomycin (Omega Scientific, Tarzana, Ca) and cultured at 37° C. with 5% $CO_2$. Additionally, to further study chondrocytic cells in a more physiologic nonadherent state, in some experiments, TC28 cells were transferred to 6 well plates that had been previously coated for 18 hours at 22° C. with 10% (v/v) in 95% ethanol solution of the cell adhesion inhibitor poly 2-hydroxyethyl methacrylate (polyHEME), followed by two washes in PBS. Complete DMEM/Ham's F12 medium was then added to the wells and the cells studied for up to 72 hours in culture (Folkman J. and Moscona A: Role of cell shape in growth control, Nature 273:345–349, 1978; Reginato A, Iozzo R, Jimenez S: Formation of Nodular Structures Resembling Mature Articular Cartilage in Long-Term Primary Cultures of Human Fetal Epiphyseal Chondrocytes on a Hydrogel Substrate, Arthritis Rheum 37: 1338–1349, 1994). Type II collagen and aggrecan expression were confirmed using RT-PCR, which verified maintenance of chondrocyte phenotype.

The chondrocyte protective effects of representative compounds were screened in vitro. The agonists included a donor of nitric oxide (NOC-12), a donor of peroxynitrite (SIN-1), and human recombinant IL-1beta. SIN-1 at 100 µM and NOC-12 at 250 µM were used as the toxic stimuli for adherent cells. In experiments using TC28 cells cultured in polyHEME plates, SIN-1 at 10 µM., NOC 12 at 25 µM and IL-1 at 10 ng/ml were used as the pro-osteorthritic triggers in the absence or presence of 1 µM of representative compound from Example 1. Cytotoxicity was studied using standard LDH release assay, and chondrocyte intracellular ATP was measured by standard luciferase assay.

The enhanced release from chondrocytes of glycosaminoglycans (GAG) is a central feature of osteoarthritic chondrocytes, and is known to be stimulated potently by IL-1, which, like NO and peroxynitrite is a major pathogenic factor in osteoarthritis. Thus, GAG release was also studied, in which, to optimize the screening assay, a one hour digestion of the cartilage "nodules" formed in the polyheme system was carried out using 300 µg/ml of papain in 20 mM sodium phosphate, 1 mM EDTA, and 2 mM DTT (pH 6.8). The digestion of the interfering proteins accomplished in this manner allowed the GAG release to be more readily detectable, and the GAG release was quantified by the standard dimethylene blue (DMB) dye binding colorimetric assay. In brief, the cell extract digested from above was combined with 46 µM DMB, 40 mM glycine and 40 mM NaCl (pH 3.0) and immediately read at 525 nm and compared again at a standard curve generated with samples of 1–50 µg/ml chondroitin sulfate (Farndale R, Buttle D, Barrett A: Improved quantitation and discrimination of sulphated glycosaminoglycans by us of dimethylmethylene blue, *Biochimica et Biophysica Acta* 883: 173–177, 1986; SztrolovicsR, White R, Poole R, Mort J, Roughley P: Resistance of small leucine-rich repeat proteoglycans to proteolytic degradation during interleukin-1 stimulated cartilage catabolism, *Biochem J.* 339: 571–577, 1999). The results of this experiment are presented in Table 2.

TABLE 2

% Decrease in GAG Release

| Compound | NOC-12 | IL-1b | SIN-1 |
|---|---|---|---|
| (1) | 27.4 | 36.8 | 47.7 |
| (2) | 50.1 | 40.9 | 23.6 |
| (3) | 28.0 | 29.1 | 21.9 |
| (4) | 17.2 | 1.5 | 11.3 |
| (5) | 14.2 | 30.7 | 35.0 |
| (6) | 11.0 | 2.4 | 1.6 |
| (7) | 46.2 | 56.6 | 42.3 |
| (8) | 32.3 | 43.8 | 55.2 |

Example 4

Further Assays Utilizing Compound (1)

Cell Viability Assay $1 \times 10^5$ TC28 cells (DMEM/F12 media with 10% FCS, 1% glutamine, 1% P/S) were plated each well in a 96 well plate and allowed to adhere overnight. The cells were washed once with PBS and media changed to contain only 1% FCS. Compound (1) at various concentrations was added to the cells for a pretreatment of 1 hr. The media was removed and fresh compound+/− the toxic stimuli were added. The cells were then incubated for 24 hrs at 37° C. Following the incubation the media was collected and used for analysis in the CytTox 96 Nonradioactive Cytotoxicity Assay (Promega, Madison, Wis.). Briefly the LDH release from the dead cells was quantified in a 30 min enzymatic reaction that results in the conversion of a tetrazolium saletin to a red formazan product. The results were then expressed as the percent of cells dead relative to the release of LDH by the control cells.

ATP Assay $5 \times 10^5$ TC28 cells were plated in a 60 mm dish and allowed to adhere overnight. The cells were then washed with PBS and media was changed to 1% FCS containing media. Compound (1) was added for 1 hr pretreatment of the cells at 37° C. The media was removed and fresh compound+/− the toxic stimuli were added and the cells incubated for 24 hrs at 37° C. The cells were gently scraped into PBS and washed and then the pellets were snap frozen in dry ice. The cells were then extracted in 0.4 N perchloric acid and incubated on ice for 15 min. The cells were centrifuged at 14,000 rpm for 15 min and the supernatant removed. 24% (by volume) of 2.2 M $KHCO_3$ was added to neutralize the solution and the precipitate was pelleted by centrifugation. This supernatant was mixed with the ATP assay mix from the Sigma ATP Luciferase kit and the reaction was counted for 15 sec (with an initial 5 sec delay) in triplicate. Counts were corrected for total DNA in the cell pellet (see Table 3).

The results of the above Cell Viability and ATP Assays are presented in Table 3, which provides the approximate $EC_{50}$ values (µM) for prevention of SIN-1 and NOC-12 mediated cell death and ATP depletion by Compound (1). In these assays, TC28 cells were pre-treated for one hour followed by 24-hour exposure to trigger in the presence of Compound (1).

TABLE 3

Preservation of Cell Viability and ATP Levels in Presence of Pro-Osteoarthritic Triggers

| | Cell Viability | | ATP Depletion | |
|---|---|---|---|---|
| Trigger | Noc12[a] | Sin-1[b] | Noc12[a] | Sin-1[b] |
| $EC_{50}$ (µM) | 0.01 | 0.01 | 0.1 | 0.1 |

[a]NOC-12 challenge: 250 µM.
[b]SIN-1 challenge: 100 µM.

Collagen Synthesis

Collagen production was measured by following $^3H$ proline incorporation as described in Johnson et al., *Arthritis Rheum.* 43:11560–70, 2000. The results are presented in Table 4, which provides the approximate $EC_{50}$ values (µM) for prevention of SIN-1, NOC-12 and IL-1 mediated GAG release (via Example 3) and inhibition of collagen synthesis (via Johnson et al.) in chondrocytes by Compound (1). In these experiments, TC28 cells in polyHEME coated plates were pre-treated for 1 hr followed by exposure to trigger for 72 hrs in the present of Compound (1).

In addition, rates of oxygen consumption by TC28 cells in monolayer culture were also evaluated by the procedures of Johnson et al., the results of which are presented in FIG. 1, which shows that Compound (1) blocked SIN-1-mediated inhibition of mitochondrial respiration in TC28 cells. In this experiment, TC28 cells were treated with 500 µM SIN-1 for 4 hr+/−10 µM Compound (1): State 3/4—basal respiration rate with no substrate addition; State 4—respiration rate in present of 5 µM/ml oligomycin; State 3U—maximal state 3 uncoupled respiration rate due to addition of the uncoupler CCCP.

TABLE 4

Matrix Preservation in Chondrocytic Cells in Presence of Pro-Osteoarthritic Triggers

| | Collagen | | | GAG Release | | |
|---|---|---|---|---|---|---|
| Trigger | Noc12[a] | Sin-1[b] | IL-1[c] | Noc12[a] | Sin-1[b] | IL-1[c] |
| $EC_{50}$ (µM) | 1 | 1 | 1 | 0.1 | 0.1 | 0.1 |

[a]NOC-12 challenge: 25 µM.
[b]SIN-1 challenge: 10 µM.
[c]IL-1 challenge: 10 ng/ml.

Bovine Cartilage Organ Culture Methods

Mature bovine knees were obtained and cartilage from the femoral condyles and patellar groove was removed in full thickness slices. (1–3 mm). Circular cores (6–7 mm in diameter) were punched out of the tissue. The cores were washed twice with media (1% FCS, 1% P/S, 1% glutamine containing DMEM high glucose) and then placed in 96 wells plates. The slices were incubated in media (as above) at 37° C. for 48 hrs to allow for recovery from the isolation process. After the recovery period, the media was removed and fresh media with Compound (1) was added to the slices for a pretreatment period of 6 hrs. Then the media was removed and fresh Compound (1)+/− IL-1 (at 10 ng/ml) was added and incubated at 37° C. for 24 hrs. The conditioned media was collected and the GAG and NO release were analyzed. Finally the slices were weighed to correct for slight variations in size or thickness. The results of this experiment are presented in Table 5, which provides the approximate $EC_{50}$ values (µM) for prevention of IL-1-mediated GAG and NO release in bovine cartilage slices by Compound (1).

TABLE 5

Prevention of Matrix Degradation and Inhibition of NO Release in Bovine Cartilage Slices in Response to IL-1 Stimulus

| | IL-1 Trigger | |
|---|---|---|
| | GAG Release | NO Release |
| $EC_{50}$ (µM) | 10 | 10 |

From the foregoing it will be appreciated that, although specific embodiments of the invention have been described herein for purposes of illustration, various modifications may be made without deviating from the spirit and scope of the invention.

What is claimed is:

1. A compound having the structure:

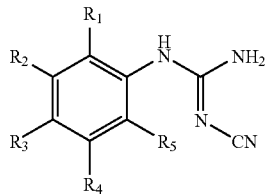

or a stereoisomer, prodrug or pharmaceutically acceptable salt thereof,
wherein
$R_1$ is methyl; and
$R_2$, $R_3$, $R_4$ and $R_5$ are the same or different and individually hydrogen, halogen, hydroxy, alkyl, alkoxy, substituted alkyl, aryl, substituted aryl, arylalky, substituted arylalkyl, heterocycle, substituted heterocycle, heterocyclealkyl or substituted heterocyclealkyl;
or $R_3$ taken together with $R_4$, or $R_4$ taken together with $R_5$, and further taken together with the respective carbon atom to which these groups are attached, form an unsubstituted or substituted fused aryl or heterocycle.

2. A compound having the structure:

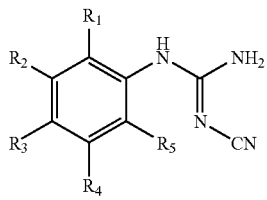

or a stereoisomer, prodrug or pharmaceutically acceptable salt thereof,
wherein
$R_1$, $R_4$ and $R_5$ are hydrogen;
$R_2$ is chlorine; and
$R_3$ is methoxy.

3. A compound having the structure:

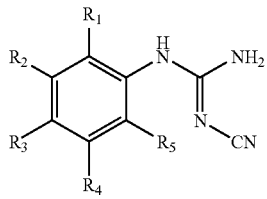

or a stereoisomer, prodrug or pharmaceutically acceptable salt thereof,
wherein
$R_1$, $R_3$ and $R_5$ are hydrogen; and
$R_2$ and $R_4$ are methyl.

* * * * *